United States Patent
Thompson et al.

(10) Patent No.: US 6,841,560 B2
(45) Date of Patent: *Jan. 11, 2005

(54) SUBSTITUTED ISOQUINOLINE DERIVATIVES AND THEIR USE AS ANTICONVULSANTS

(75) Inventors: Mervyn Thompson, Harlow (GB); Robert William Ward, Great Dunmow (GB); Peter David Edwards, Horsham (GB)

(73) Assignee: SmithKline Beecham p.l.c., Brentford (GB)

( * ) Notice: Subject to any disclaimer, the term of this patent is extended or adjusted under 35 U.S.C. 154(b) by 27 days.

This patent is subject to a terminal disclaimer.

(21) Appl. No.: 10/353,498

(22) Filed: Jan. 29, 2003

(65) Prior Publication Data

US 2003/0144320 A1 Jul. 31, 2003

Related U.S. Application Data

(63) Continuation of application No. 09/840,786, filed on Apr. 24, 2001, now abandoned, which is a continuation of application No. 09/381,408, filed as application No. PCT/GB98/00782 on Mar. 16, 1998, now abandoned.

(30) Foreign Application Priority Data

Mar. 18, 1997 (GB) .............................................. 9705619
Dec. 17, 1997 (GB) .............................................. 9726695

(51) Int. Cl.$^7$ ...................... A61K 31/47; C07D 217/22; A07D 401/00
(52) U.S. Cl. .......................... 514/310; 546/143; 546/148
(58) Field of Search ........................... 514/310; 546/143, 546/148

(56) References Cited

U.S. PATENT DOCUMENTS 4,022,900 A * 5/1977 Mathison ..................... 514/307
6,274,594 B1 * 8/2001 Coulton et al. .............. 514/308
6,492,388 B1 * 12/2002 Harling et al. .............. 514/310

FOREIGN PATENT DOCUMENTS

DE          2101691       * 3/1972
WO       WO 97/48683        12/1997
WO       WO 9748683      * 12/1997

OTHER PUBLICATIONS

Mathison, CA 84:25770, 1975.*
Mathison, CA 82:25682, 1974.*
Mathison, et al., "Synthesis and Hypotensive Properties of Tetrahydroisoquinolines", (1973), Journal of Medicinal Chemistry, 16(4), pp. 332–336.

* cited by examiner

Primary Examiner—D. Margaret Seaman
(74) Attorney, Agent, or Firm—Linda E. Hall; Stephen Venetianer; Charles M. Kinzig

(57) ABSTRACT

This invention relates to substituted isoquinoline derivatives and their use as anticonvulsants.

11 Claims, No Drawings

SUBSTITUTED ISOQUINOLINE DERIVATIVES AND THEIR USE AS ANTICONVULSANTS

This is a continuation of prior application Ser. No: 09/840,786, filed Apr. 24, 2001; now abandoned which is a continuation of application Ser. No: 09/381,408, filed Sep. 17, 1999; now abandoned which is a 371 application of International Application No. PCT/GB98/00782, filed 16 Mar. 1998; which claims the benefit of priority from Great Britain Application Nos. GB9705619.6, filed 18 Mar. 1997 and GB9726695.1, filed 17 Dec. 1997.

This invention relates to novel compounds, to processes for preparing them, and to their use as therapeutic agents.

WO97/48683 (SmithKline Beecham), unpublished at the filing date of this application, discloses tetrahydroisoquinolinyl benzamides in which the benzamide moiety has a 2-alkoxy substituent, including the compounds: N-(7-iodo-2-methyl-1,2,3,4-tetrahydroisoquinolin-5-yl)-5-benzoyl-2-methoxybenzamide, N-(7-iodo-1,2,3,4-tetrahydroisoquinolin-5-yl)-5-benzoyl-2-methoxybenzamide, N-(5-iodo-1,2,3,4-tetrahydroisoquinolin-7-yl)-5-benzoyl-2-methoxybenzamide, N-(5-iodo-1,2,3,4-tetrahydroisoquinolin-7-yl)-2-methoxy-4-trifluoromethyldiazirinylbenzamide, N-(5-iodo-1,2,3,4-tetrahydroisoquinolin-7-yl)-2-methoxy-5-trifluoromethyldiazirinyl-benzamide, N-(7-iodo-1,2,3,4-tetrahydroisoquinolin-5-yl)-2-methoxy-5-trifluoromethyldiazirinyl-benzamide and N-(8-fluoro-2-methyl-1,2,3,4-tetrahydroisoquinolin-5-yl)-4-t-butyl-2-methoxybenzamide.

It has now been surprisingly found that carboxamide compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction and amyotrophic lateral sclerosis (ALS).

Accordingly, the present invention provides a compound of formula (I) or pharmaceutically acceptable salt thereof:

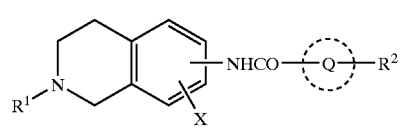

(I)

where Q is a monocyclic or bicyclic aryl or heteroaryl ring,
$R^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO_2$—, $R^2$ is hydrogen, hydroxy, or up to three substituents selected from halogen, $NO_2$, CN, $N_3$, $CF_3O$—, $CF_3S$—, $CF_3CO$—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, acetoxy, phenyl, phenoxy, benzyloxy, benzoyl, phenyl-$C_{1-4}$alkyl-, $C_{1-6}$alkylS—, $C_{1-6}$alkylSO_2$—, $(C_{1-4}$alkyl$)_2$NSO_2$—, $(C_{1-4}$alkyl$)$NHSO_2$—, $(C_{1-4}$alkyl$)_2$NCO—, $(C_{1-4}$alkyl$)$NHCO— or $CONH_2$;
or —$NR^3R^4$ where $R^3$ is hydrogen or $C_{1-4}$alkyl, and $R^4$ is hydrogen, $C_{1-4}$alkyl, formyl, —$CO_2C_{1-4}$alkyl or —$COC_{1-4}$alkyl; or two $R^2$ groups together form a carbocyclic ring that is saturated or unsaturated and unsubstituted or substituted by —OH or =O; and
X is hydrogen, halogen, $C_{1-6}$ alkoxy, $C_{1-6}$alkyl, amino or trifluoroacetylamino; but when X is hydrogen excluding compounds in which $R^2$ is 2-alkoxy and when X is halogen excluding the compounds N-(7-iodo-2-methyl-1,2,3,4-tetrahydroisoquinolin-5-yl)-5-benzoyl-2-methoxybenzamide, N-(7-iodo-1,2,3,4-tetrahydroisoquinolin-5-yl)-5-benzoyl-2-methoxybenzamide, N-(5-iodo-1,2,3,4-tetrahydroisoquinolin-7-yl)-5-benzoyl-2-methoxybenzamide, N-(5-iodo-1,2,3,4-tetrahydroisoquinolin-7-yl)-2-methoxy-4-trifluoromethyldiazirinylbenzamide, N-(5-iodo-1,2,3,4-tetrahydroisoquinolin-7-yl)-2-methoxy-5-trifluoromethyldiazirinylbenzamide, N-(7-iodo-1,2,3,4-tetrahydroisoquinolin-5-yl)-2-methoxy-5-trifluoromethyldiazirinylbenzamide and N-(8-fluoro-2-methyl-1,2,3,4-tetrahydroisoquinolin-5-yl)-4-t-butyl-2-methoxybenzamide.

The compounds of this invention are typically, (tetrahydroisoquinolin-7-yl) carboxamides, especially (tetrahydroisoquinolin-7-yl)benzamides. When the substituent X is not hydrogen it may be at the 5, 6, or 8 position of the tetrahydroisoquinoline moiety, especially position 5.

The ring system Q is typically optionally substituted phenyl or optionally substituted heteroaryl, typically thiophenyl or 3-isoxazolyl. When two $R^2$ groups form a carbocyclic ring, this is typically a 5–7 membered ring, and Q may be a naphthalene or an indane or indanone ring system or a bicyclic heteroaryl such as 5-dihydrobenzofuranyl.

In the formula (I), alkyl groups, including alkyl groups that are part of other moieties, such as alkoxy or acyl, may be straight chain or branched. Phenyl groups, including phenyl groups that are part of other moieties, in $R^2$ may optionally be substituted with one or more independently selected from halogen or $C_{1-6}$alkyl, $C_{1-6}$alkoxy or $C_{1-6}$alkylcarbonyl.

Suitable $C_{3-6}$cycloalkyl groups include cyclopropyl, cyclobutyl, cyclopentyl, and cyclohexyl. Suitable halo substituents include fluoro, chloro, iodo and bromo.

One suitable group of compounds of this invention are of formula (IA)

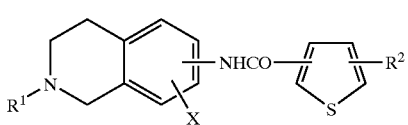

(IA)

and another suitable group are of formula (IB)

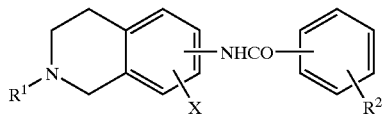

(IB)

A suitable group of compounds of formula (I) have $R^1$ as hydrogen, methyl, ethyl propyl, hydroxyethyl, methoxyethyl, formyl, acetyl, trifluoroacetyl or methanesulfonyl, $R^2$ as hydrogen or one or more of methyl, ethyl, n-butyl, iso-propyl, iso-butyl, t-butyl, phenyl, methoxy, ethoxy, iso-propoxy, n-butoxy, cyclopropylmethoxy, phenoxy, benzyloxy, amino, acetylamino, nitro, azido, cyano, bromo, chloro, fluoro, iodo, acetyl, pivaloyl, iso-butyroyl, benzoyl, iodobenzoyl, trifluoromethyl, perfluoroethyl, trifluoromethoxy, trifluoroacetyl, trifluoromethyldiazirinyl, methanesulfonyl, n-propylsulfonyl, isopropylsulfonyl, dimethylsulfamoyl;

or two groups $R^2$ form a benzene, cyclopentane or cyclopentanone ring;

X as hydrogen, chloro, bromo, iodo, fluoro, amino, trifluoroacetylamino.

A preferred group of compounds of formula (I) have $R^1$ as hydrogen, methyl, methoxyethyl, $R^2$ as hydrogen or one or more of methyl, n-butyl, t-butyl, iso-propyl, phenyl, methoxy, ethoxy, iso-propoxy, phenoxy, acetyl, nitro, cyano, bromo, chloro, fluoro, iodo, pivaloyl trifluoromethyl, azido, trifluoromethoxy.

X as hydrogen, iodo, chloro, bromo or trifluoroacetylamino.

Examples of compounds of formula (I) are:

N-(1,2,3,4-tetrahydroisoquinolin-7-yl)-5-chlorothiophene-2-carboxamide
N-(2-methyl-1,2,3,4-tetrahydroisoquinolin-7-yl)-5-chlorothiophene-2-carboxamide
N-(2-methyl-1,2,3,4-tetrahydroisoquinolin-7-yl)benzamide
N-(2-methyl-1,2,3,4-tetrahydroisoquinolin-7-yl)-3-chlorobenzamide
N-(2-methyl-1,2,3,4-tetrahydroisoquinolin-7-yl)-4-t-butylbenzamide
N-(2-methyl-1,2,3,4-tetrahydroisoquinolin-7-yl)-4-iso-propoxybenzamide
N-(2-methyl-1,2,3,4-tetrahydroisoquinolin-7-yl)-4-phenoxybenzamide
N-(2-methyl-1,2,3,4-tetrahydroisoquinolin-7-yl)-4-nitrobenzamide
N-(2-methyl-1,2,3,4-tetrahydroisoquinolin-7-yl)-4-phenylbenzamide
N-(2-methyl-1,2,3,4-tetrahydroisoquinolin-7-yl)-3-methylbenzamide
N-(2-methyl-1,2,3,4-tetrahydroisoquinolin-7-yl)-3-fluorobenzamide
N-(2-methyl-1,2,3,4-tetrahydroisoquinolin-7-yl)-3-cyanobenzamide
N-(2-methyl-1,2,3,4-tetrahydroisoquinolin-7-yl)-3,4-dichlorobenzamide
N-(2-methyl-1,2,3,4-tetrahydroisoquinolin-7-yl)-4-iodobenzamide
N-(2-methyl-1,2,3,4-tetrahydroisoquinolin-7-yl)-4-bromobenzamide
N-(2-methyl-1,2,3,4-tetrahydroisoquinolin-7-yl)-4-methylbenzamide
N-(2-methyl-1,2,3,4-tetrahydroisoquinolin-7-yl)-3-nitrobenzamide
N-(2-methyl-1,2,3,4-tetrahydroisoquinolin-7-yl)-4-ethoxybenzamide
N-(2-methyl-1,2,3,4-tetrahydroisoquinolin-7-yl)-4-n-butylbenzamide
N-(2-methyl-1,2,3,4-tetrahydroisoquinolin-7-yl)-2-acetoxybenzamide
N-(2-methyl-1,2,3,4-tetrahydroisoquinolin-7-yl)-3-trifluoromethylbenzamide
N-(2-methyl-1,2,3,4-tetrahydroisoquinolin-7-yl)-2,4-difluorobenzamide
N-(2-methyl-1,2,3,4-tetrahydroisoquinolin-7-yl)-3,4-dimethoxybenzamide
N-(2-methyl-1,2,3,4-tetrahydroisoquinolin-7-yl)-2-fluoro-4-trifluoromethylbenzamide
N-(2-methyl-1,2,3,4-tetrahydroisoquinolin-7-yl)-4-chloro-3-nitrobenzamide
N-(2-methyl-1,2,3,4-tetrahydroisoquinolin-7-yl)-3,5-di-trifluoromethylbenzamide
N-(2-methyl-1,2,3,4-tetrahydroisoquinolin-7-yl)-2,4-dichloro-5-fluorobenzamide
N-(2-methyl-1,2,3,4-tetrahydroisoquinolin-7-yl)-3-fluoro-5-trifluoromethylbenzamide
N-(2-methyl-1,2,3,4-tetrahydroisoquinolin-7-yl)-3-bromo-4-methoxybenzamide
N-(2-methyl-1,2,3,4-tetrahydroisoquinolin-7-yl)-3,4,5-trimethoxybenzamide
N-(2-methyl-1,2,3,4-tetrahydroisoquinolin-7-yl)-4-trifluoromethoxybenzamide
N-(2-methyl-1,2,3,4-tetrahydroisoquinolin-7-yl)-3-pivaloylbenzamide
N-(2-Methyl-1,2,3,4-tetrahydroisoquinolin-7-yl)-3-bromo-4-iso-propoxybenzamide
N-(2-Methyl-1,2,3,4-tetrahydroisoquinolin-7-yl)-4-acetoxybenzamide
N-(2-Methyl-1,2,3,4-tetrahydroisoquinolin-7-yl)-4-cyclopentyloxybenzamide
N-(2-methyl-1,2,3,4-tetrahydroisoquinolin-7-yl)-4-cyclopropylmethoxybenzamide
N-(2-Methyl-1,2,3,4-tetrahydroisoquinolin-7-yl)-3-cyano-4-methoxybenzamide
N-(2-Methyl-1,2,3,4-tetrahydroisoquinolin-7-yl)-2-naphthamide
N-(2-Methyl-1,2,3,4-tetrahydroisoquinolin-7-yl)-3-bromo-4-methylbenzamide
N-(2-Methyl-1,2,3,4-tetrahydroisoquinolin-7-yl)-naphthalene-1-carboxamide
N-(2-Methyl-1,2,3,4-tetrahydroisoquinolin-7-yl)-3-chloro-4-methoxybenzamide
N-(2-Methyl-1,2,3,4-tetrahydroisoquinolin-7-yl)-4-tert-butoxybenzamide
N-(2-Methyl-1,2,3,4-tetrahydroisoquinolin-7-yl)-4-n-propoxybenzamide
N-(2-Methyl-1,2,3,4-tetrahydroisoquinolin-7-yl) benzotriazole-5-carboxamide
N-(2-Methyl-1,2,3,4-tetrahydroisoquinolin-7-yl) benzothiazole-6-carboxamide
N-(2-Methyl-1,2,3,4-tetrahydroisoquinolin-7-yl)-2,3-dihydrobenzofuran-5-carboxamide N-(2-Methyl-1,2,3,4-tetrahydroisoquinolin-7-yl)-2-methylbenzimidazole-5-carboxamide
N-(2-Methyl-1,2,3,4-tetrahydroisoquinolin-7-yl)-3-chloro-4-iso-propoxybenzamide
N-(2-Methyl-1,2,3,4-tetrahydroisoquinolin-7-yl)-3-bromo-4-ethoxybenzamide
N-(2-Methyl-1,2,3,4-tetrahydroisoquinotin-7-yl)-3-chloro-4-ethoxybenzamide
N-(2-Methyl-1,2,3,4-tetrahydroisoquinolin-7-yl)-4-methoxy-3-trifluoromethyl benzamide
N-(2-Methyl-1,2,3,4-tetrahydroisoquinolin-7-yl)-3,5-dichloro-4-methoxybenzamide
N-(2-Methyl)-1,2,3,4-tetrahydroisoquinolin-7-yl)-3,5-dichloro-4-ethoxybenzamide
N-(2-Methyl)-1,2,3,4-tetrahydroisoquinolin-7-yl)-3,5-dichloro-4-iso-propoxybenzamide
N-(2-Methyl-1,2,3,4-tetrahydroisoquinolin-7-yl)-3-methylsulfonylbenzamide
N-(2-methyl-1,2,3,4-tetrahydroisoquinolin-7-yl)-3-bromo-4-tert-butylbenzamide
N-(2-Methyl-1,2,3,4-tetrahydroisoquinolin-7-yl)-2-bromo-5-methoxybenzamide
N-(2-Methyl-1,2,3,4-tetrahydroisoquinolin-7-yl)-4-fluoro-3-methoxybenzamide, hydrochloride
N-(2-Methyl-1,2,3,4-tetrahydroisoquinolin-7-yl)-1-methylpyrazole-4-carboxamide
N-(2-Methyl-1,2,3,4-tetrahydroisoquinolin-7-yl)-4-trifluoromethylpyrazole-3-carboxamide
N-(2-Methyl-1,2,3,4-tetrahydroisoquinolin-7-yl)-2-methylthiazole-4-carboxamide
N-(2-Methyl-1,2,3,4-tetrahydroisoquinolin-7-yl)-5-methylisoxazole-3-carboxamide
N-(2-Methyl-1,2,3,4-tetrahydroisoquinolin-7-yl)-5-tert-butylisoxazole-3-carboxamide
N-(2-Methyl-1,2,3,4-tetrahydroisoquinolin-7-yl)-3-methoxyisoxazole-5-carboxamide hydrochloride
N-(2-methyl-1,2,3,4-tetrahydroisoquinolin-7-yl)indole-2-carboxamide.
N-(2-Methyl-1,2,3,4-tetrahydroisoquinolin-7-yl)-3-bromo-4-iso-propylbenzamide, hydrochloride
N-(2-Methyl-1,2,3,4-tetrahydroisoquinolin-7-yl)-3-cyano-4-iso-propylbenzamide, hydrochloride
N-(2-Methyl-1,2,3,4-tetrahydroisoquinolin-7-yl)-3-fluoro-4-methoxybenzamide
N-(2-Methyl-1,2,3,4-tetrahydroisoquinolin-7-yl)-3-cyano-4-n-propoxybenzamide
N-(2-Methyl-1,2,3,4-tetrahydroisoquinolin-7-yl)-3-cyano-4-ethoxybenzamide
N-(2-Methyl-1,2,3,4-tetrahydroisoquinolin-7-yl)-3-bromo-4-n-propoxybenzamide
N-(2-Methyl-1,2,3,4-tetrahydroisoquinolin-7-yl)-3-bromo-4-ethylbenzamide
N-(2-Methyl-1,2,3,4-tetrahydroisoquinolin-7-yl)-3-iodo-4-methoxybenzamide
N-(2-Methyl-1,2,3,4-tetrahydroisoquinolin-7-yl)-4-iso-propoxy-3-trifluoromethylbenzamide
N-(2-Methyl-1,2,3,4-tetrahydroisoquinolin-7-yl)-4-chloro-3-methoxybenzamide
N-(2-Methyl-1,2,3,4-tetrahydroisoquinolin-7-yl)-4-n-propoxy-3-trifluoromethylbenzamide
N-(2-Methyl-1,2,3,4-tetrahydroisoquinolin-7-yl)-3-chloro-4-tert-butylbenzamide, hydrochloride
N-(2-Methyl-1,2,3,4-tetrahydroisoquinolin-7-yl)-4-methoxybenzamide hydrochloride.
N-(2-Methyl-1,2,3,4-tetrahydroisoquinolin-7-yl)-4-fluoro-3-methylsulfonylbenzamide, hydrochloride
N-(2-Methyl-1,2,3,4-tetrahydroisoquinolin-7-yl)-3-chloro-4-iso-propylbenzamide
N-(2-Methyl-1,2,3,4-tetrahydroisoquinolin-7-yl)-3-cyano-4-ethylbenzamide hydrochloride
N-(2-Methyl-1,2,3,4-tetrahydroisoquinolin-7-yl)-4-iso-propyl-3-trifluoromethylbenzamide hydrochloride
N-(2-Methyl-1,2,3,4-tetrahydroisoquinolin-7-yl)-4-ethyl-3-trifluoromethylbenzamide hydrochloride
N-(2-Methyl-1,2,3,4-tetrahydroisoquinolin-7-yl)-3-cyano-4-iso-propoxybenzamide hydrochloride
N-(1,2,3,4-Tetrahydroisoquinolin-7-yl)-4-methoxy-3-trifluoromethylbenzamide
N-(2-Methyl-1,2,3,4-tetrahydroisoquinolin-7-yl)-4-methyl-3-methylsulfonyl-benzamide
N-(2-Methyl-1,2,3,4-tetrahydroisoquinolin-7-yl)-4-ethyl-3-methylsulfonylbenzamide
N-(2-Methyl-1,2,3,4-tetrahydroisoquinolin-7-yl)-3-methylsulfonyl-4-iso-propylbenzamide
N-(2-Methyl-1,2,3,4-tetrahydroisoquinolin-7-yl)-3-methylsulfonyl-4-methoxybenzamide
N-(2-Methyl-1,2,3,4-tetrahydroisoquinolin-7-yl)-3-trifluoroacetylbenzamide, hydrochloride
N-(2-Methyl-1,2,3,4-tetrahydroisoquinolin-7-yl)-4-methoxy-3-pentafluoroethylbenzamide hydrochloride
N-(2-n-Propyl-1,2,3,4-tetrahydroisoquinolin-7-yl)-3-bromo-4-ethoxybenzamide
N-(2-n-Propyl-1,2,3,4-tetrahydroisoquinolin-7-yl)-4-methoxy-3-trifluoromethylbenzamide
N-(2-n-Propyl-1,2,3,4-tetrahydroisoquinolin-7-yl)-3-chloro-4-iso-propoxybenzamide
N-(2-Methyl-1,2,3,4-tetrahydroisoquinolin-7-yl)-3-cyano-4-iso-butylbenzamide hydrochloride
N-(2-Methyl-1,2,3,4-tetrahydroisoquinolin-7-yl)-4-iso-butyl-3-trifluoromethylbenzamide hydrochloride
N-(2-Ethyl-1,2,3,4-tetrahydroisoquinolin-7-yl)-3-bromo-4-ethoxybenzamide
N-(2-Ethyl-1,2,3,4-tetrahydro-isoquinolin-7-yl)-4-methoxy-3-trifluoromethylbenzamide
N-(2-iso-Propyl-1,2,3,4-tetrahydroisoquinolin-7-yl)-3-bromo-4-ethoxybenzamide
N-(2-iso-Propyl-1,2,3,4-tetrahydroisoquinolin-7-yl)-4-methoxy-3-trifluoromethylbenzamide
N-(2-Methyl-1,2,3,4-tetrahydroisoquinolin-7-yl)-4-ethoxy-3-methylsulfonyl-benzamide
N-(2-Methyl-1,2,3,4-tetrahydroisoquinolin-7-yl)-4-oxochroman-6-carboxamide hydrochloride
N-(2-Formyl-1,2,3,4-tetrahydroisoquinolin-7-yl)-4-methoxy-3-trifluoromethylbenzamide
N-(2-Hydroxyethyl-1,2,3,4-tetrahydroisoquinolin-7-yl)-3-bromo-4-ethoxybenzamide
N-(2-Hydroxyethyl-1,2,3,4-tetrahydroisoquinolin-7-yl)-3-bromo-4-ethylbenzamide
N-(2-Methyl-1,2,3,4-tetrahydroisoquinolin-7-yl)-4-phenylmethoxy-3-trifluoromethylbenzamide
N-(2-Methyl-1,2,3,4-tetrahydroisoquinolin-7-yl)-4-hydroxy-3-trifluoromethylbenzamide
N-(2-Methoxyethyl-1,2,3,4-tetrahydroisoquinolin-7-yl)-3-bromo-4-iso-propoxybenzamide
N-(2-Methoxyethyl-1,2,3,4-tetrahydroisoquinolin-7-yl)-3-chloro-4-iso-propoxybenzamide
N-(2-Methoxyethyl-1,2,3,4-tetrahydroisoquinolin-7-yl)-4-methoxy-3-trifluoromethylbenzamide
N-(5-Iodo-1,2,3,4-tetrahydroisoquinolin-7-yl)-4-azidobenzamide, trifluoroacetate
N-(2-Methyl-5-trifluoroacetylamino-1,2,3,4-tetrahydroisoquinolin-7-yl)-3-bromo-4-methoxybenzamide
N-(2-Methyl-5-chloro-1,2,3,4-tetrahydroisoquinolin-7-yl)-3-bromo-4-ethoxybenzamide N-(2-Methyl-5-chloro-1,2,3,4-tetrahydroisoquinolin-7-yl)-3-bromo-4-ethylbenzamide When synthesised, these compounds are often in salt form, such as the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colorants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction and amyotrophic lateral sclerosis (ALS) which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction and amyotrophic lateral sclerosis (ALS) comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction and amyotrophic lateral sclerosis (ALS).

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction and amyotrophic lateral sclerosis (ALS).

Another aspect of the invention is a process for the preparation of compounds of formula (I), which comprises reacting a compound of formula (II)

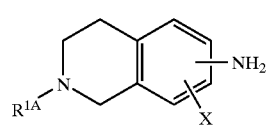

(II)

where $R^{1A}$ is $R^1$ as defined for formula (I) or a group convertible to $R^1$ and X is as defined in claim 1 with a compound of formula (III)

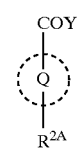

(III)

where Q is as defined in formula (I), Y is Cl or OH, and $R^{2A}$ groups are independently $R^2$ as defined for formula (I) or groups convertible to $R^2$, and where required converting an $R^{1A}$ or $R^{2A}$ group to a $R^1$ or $R^2$ group, converting one $R^1$ or $R^2$ group to another $R^1$ or $R^2$ group, converting a salt product to the free base or another pharmaceutically acceptable salt or converting a free base product to a pharmaceutically acceptable salt.

Reaction of a compound of formula (III) which is an acid chloride (Y=Cl) will lead directly to the hydrochloride salt. Suitable solvents include ethyl acetate or dichloromethane, optionally in the presence of a base such as triethylamine. When the compound of formula (III) is an aromatic acid (Y=OH), conventional conditions for condensation of such acids with amines may be used, for example reacting the components in a mixture of (dimethylaminopropyl)-ethyl-carbodiimide/hydroxybenzotriazole in a suitable solvent such as dimethyl formamide.

Conversions of an $R^{1A}$ or $R^{2A}$ group to a $R^1$ or $R^2$ group typically arise when a protecting group is needed during the above coupling reaction or during the preparation of the reactants by the procedures described below. Interconversion of one $R^1$ or $R^2$ group to another typically arises when one compound of formula (I) is used as the immediate precursor of another compound of formula (I) or when it is easier to introduce a more complex or reactive substituent at the end of a synthetic sequence.

Compounds of formula (II) in which X is hydrogen may be prepared from a nitro-tetrahydroisoquinoline of formula (IV).

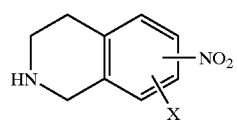

(IV)

by reaction with a compound $R^{1A}Z$ where Z is a leaving group such as halogen, especially iodo, or tosylate to obtain an intermediate of formula (V)

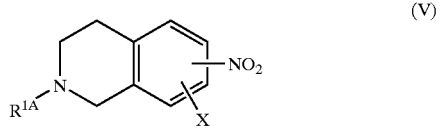

which can be reduced, for example using either tin (II) chloride and HCL or hydrogen and a palladium/activated carbon catalyst, to obtain an amino-tetrahydroisoquinoline of formula (II).

When the intended $R^{1A}$ group is methyl, the compound of formula (IV) may also be reacted with formic acid and formaldehyde to introduce the N-methyl group.

The nitro-tetrahydroisoquinoline of formula (IV) may be prepared by hydrolysis of 2-trifluoroacetyl-nitro-tetrahydroisoquinoline obtained by reaction of an N-(nitrophenyl)ethyl-trifluoroacetamide and paraformaldehyde in acidic conditions using the procedure of Stokker, Tet. Lett., 1996, 37, 5453. N-(nitrophenyl)ethyl-trifluoroacetamides can be prepared from readily available materials by reaction of trifluoracetic anhydride with lutidine and nitrophenethylamine hydrochloride, as illustrated in the Descriptions below.

Compounds of formula (II) may also be prepared from the corresponding amino-isoquinoline (or its nitro-analogue) of formula (VI)

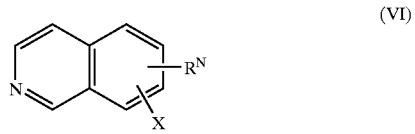

where $R^N$ is $NH_2$ or $NO_2$ by reaction with a compound $R^{1A}Z$ where Z is a leaving group such as halogen, especially iodo, or tosylate to obtain an intermediate of formula (VII)

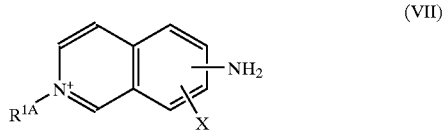

which can be reduced, for example using sodium borohydride, or hydrogenated, for example using hydrogen and a palladium/activated carbon catalyst, to obtain a tetrahydroisoquinoline of formula (II). When the compound of formula (VII) is replaced by a nitro-isoquinoline, the nitro group is converted to an amino group in the hydrogenation step.

When the intended $R^1$ is hydrogen, the N of the tetrahydroisoquinoline or isoquinoline is preferably protected conventionally, prior to the coupling step that forms the carboxamide of formula (I), for example by tert.-butoxycarbonyl or trifluoroacetyl. The compound can be deprotected under standard conditions, for example using trifluoroacetic acid/methylene chloride.

Amino/nitro-isoquinolines of formulae (VI) and the reagents used are commercially available, or can be prepared from commercially available materials using conventional procedures described in the literature.

When the substituent X is other than hydrogen it may be introduced during any of the procedures above, for example by conventional substitution of the aromatic ring of compounds of formula (IV), (V) or (VII) or may be present on commercially available starting materials usable in the above described procedures. Most suitably the substituent X is introduced to a compound of formula (II) in which X is hydrogen. For example X as halogen may be incorporated via an amino group using Sandmeyer chemistry as illustrated in the descriptions below.

Compounds of formula (III) may be prepared by further substitution of commercially available benzoic acid or thiophene carboxylic acid derivatives using conventional procedures, or by oxidation of corresponding substituted benzyl alcohols. Alternatively benzoic acids can be prepared from correspondingly substituted phenols, for example by formation of the acetate, conversion to an acetophenone and then to the desired acid.

Where the above described intermediates are novel compounds, they also form part of this invention.

The preparation of compounds of this invention is further illustrated by the following Descriptions and Examples. The utility of compounds of this invention is shown by the Pharmacological Data that follow the Examples.

DESCRIPTION 1

N-2-(4-Nitrophenyl)ethyl-trifluoroacetamide

A solution of trifluoroacetic anhydride (10.6 ml) in dichloromethane (100 ml) was added dropwise to a stirred solution of 2,6-lutidine (17.44 ml) and 4-nitrophenethylamine hydrochloride (15.2 g; 75 mmol) at 0° C. The mixture was stirred at 25° C. overnight under argon and then washed with dilute citric acid (×2), brine and dried over $Na_2SO_4$. The material in the organic phase gave the title compound as a pale yellow solid (19.04 g).

DESCRIPTION 2

7-Nitro-1,2,3,4-tetrahydro-2-trifluoroacetylisoquinoline

The nitro compound D1 (2.26 g; 9.15 mmol) and paraformaldehyde (0.45 g; 14.4 mmol) in acetic acid (10 ml) and conc. $H_2SO_4$ (15 ml) were stirred at 25° C. for 20 h according to the procedure of G. E. Stokker., Tet. Lett., 1996, 37, 5453. Work up afforded the title compound as a white solid (2.17 g).

$^1$H NMR (CDCl$_3$) δ: 3.10 (2H, m), 3.92 (2H, m), 4.85+ 4.92 (2H, 2xs), 7.38 (1H, t), 8.10 (2H, m); m/z (EI): 274 (M$^+$).

DESCRIPTION 3

7-Nitro-1,2,3,4-tetrahydroisoquinoline

The trifluoroacetamide D2 (17.22 g; 63 mmol) was hydrolysed at room temperature using a solution of potassium carbonate (46.6 g) in 10% aqueous methanol (660 ml). Work-up with dichloromethane gave the title compound (11 g).

DESCRIPTION 4

2-Methyl-7-nitro-1,2,3,4-tetrahydroisoquinoline

The amine D3 (2.08 g; 11.7 mmol) was treated with 88% formic acid (3.45 ml) and 37% aqueous formaldehyde (5.88 ml) at 80° C. for 2 h according to the procedure of G. M. Carrera and D. S. Garvey, J. Het. Chem., 1992, 29, 847. Basification with 10% sodium hydroxide followed by work-up with ethyl acetate afforded an orange gum(2.3 g). Chromatography on Kiesegel 60 in 0–3% methanol-ethyl acetate gave the title compound as an orange solid (1.7 g).

m/z (CI): 193 (MH$^+$).

DESCRIPTION 5

7-Amino-2-methyl-1,2,3,4-tetrahydroisoquinoline

The 7-nitro compound D4 (0.25 g; 1.3 mmol) in methanol (40 ml) was hydrogenated over 10% palladium on carbon (100 mg) at atmospheric pressure overnight. The catalyst was removed by filtration through a pad of Kieselguhr and evaporation in vacuo gave the title compound as a white solid (213 mg).

m/z (CI): 163 (MH$^+$).

DESCRIPTION 6

7-Amino-2-(t-butyloxycarbonyl)-1,2,3,4-tetrahydroisoquinoline

The title compound was prepared from the compound of Description D3 using di t-butyl dicarbonate in 10% aqueous hydroxide in dioxan at 25° C. followed by catalytic hydrogenation according to the procedure described for D5.

DESCRIPTION 7

N-(2-t-Butyloxycarbonyl-1,2,3,4-tetrahydroisoquinoline-7-yl)-5-chlorothiophene-2-carboxamide 5-Chlorothiophene-2-carboxylic acid (214 mg; 1.3 mmol), ethyldimethylaminopropyl carbodiimide (250 mg; 1.3 mmol) and 1-hydroxybenzotriazole (176 mg; 1.3 mmol) in dry DMF (25 ml) was stirred at room temperature for 30 min. A solution of the N-boc amine D6 (300 mg; 1.21 mmol) in dichloromethane (5 ml) was added and the mixture kept at room temperature overnight. Work-up gave a pink gum which was chromatographed on Kieselgel 60 in 30% ethyl acetate-hexane. Combination of appropriate fractions gave the title compound as an off white solid (0.5 g).

$^1$H NMR (400 MHz, CDCl$_3$) δ: 1.51 (9H, s), 2.82 (2H, t), 3.65 (2H, t), 4.56 (2H, s), 6.95 and 7.37 (2H, ABq), 7.12 (1H, d), 7.28 (1H, s), 7.46 (1H, br).

DESCRIPTION 8

7-Nitro-2-n-propyl-1,2,3,4-tetrahydroisoquinoline

Nitro compound D3 (1.55 g, 8.7 mmol) and propionaldehyde (2.52 g, 43.5 mmol) in 1,2-dichloroethane (50 ml) were treated with sodium triacetoxyborohydride (0.28 g, 13.1 mmol) and glacial acetic acid (0.6 ml, 9.0 mmol). The mixture was stirred at 25° C. over the weekend and then diluted with dichloromethane (50 ml). The mixture was washed with saturated NaHCO$_3$, dried (Na$_2$SO$_4$) and evaporated in vacuo. Chromatography on Kieselgel 60 in ethyl acetate gave the title compound.

DESCRIPTION 9

7-Amino-2-n-propyl-1,2,3,4-tetrahydroisoquinoline

The nitro compound D8 (0.73 g, 3.32 mmol) in ethanol (100 ml) was heated to 50° C. and treated with a solution of tin (II) chloride (2.52 g, 13.27 mmol) in conc. HCl (10 ml) and stirring continued for 3 h. The mixture was basified with 40% NaOH and the product extracted into dichloromethane. Work-up and chromatography on Kieselgel 60 in 10% methanol:dichloromethane gave the title compound as a viscous yellow oil (0.26 g; 41%).

m/z (API$^+$): 191 (MH$^+$; 80%).

DESCRIPTION 10

7-Amino-2-iso-propyl-1,2,3,4-tetrahydroisoquinoline

The title compound was prepared from D3 and acetone in 10% overall yield using a method similar to that described in Descriptions 8 and 9.

DESCRIPTION 11

7-Amino-2-ethyl-1,2,3,4-tetrahydroisoquinoline

The title compound was prepared in 14% overall yield from D3 and acetaldehyde using a method similar to that described in Descriptions 5 and 8.

DESCRIPTION 12

2-Formyl-7-nitro-1,2,3,4-tetrahydroisoquinoline

A mixture of acetic anhydride (1.4 ml) and formic acid (0.7 ml) was stirred at 50° C. for 15 min. After cooling to 0° C., a solution of D3 (1.78 g) and 4-dimethylaminopyridine (0.1 g) in dichloromethane (30 ml) was added and stirring continued at 25° C. for 2 h. The reaction mixture was washed with aq. potassium carbonate, water, brine and dried (MgSO$_4$). Evaporation in vacuo gave the title compound (2.4 g).

$^1$H NMR (250 MHz, CDCl$_3$) δ: 3.0 (2H, m), 3.72 (t) and 3.88 (t) (together 2H), 4.68 (t) and 4.80 (t) (together 2H), 7.28–7.40 (1H, m), 8.04 (2H, m), 8.22 (s) and 8.30 (s) (together 1H), m/z (API$^+$): 207 (MH$^+$: 80%).

DESCRIPTION 13

7-Amino-2-formyl-1,2,3,4-tetrahydroisoquinoline

The compound D12 (2.3 g) was dissolved in ethanol (50 ml) and shaken at room temperature and 50 psi with hydrogen in the presence of 5% Pd/C catalyst (0.8 g). Filtration and evaporation then provided the title compound as a white solid (1.6 g).

$^1$H NMR (250 MHz, d$_6$-DMSO) δ: 2.55 (t) and 2.59 (t) (together 2H) 3.56 (2H, t), 3.39 (s) and 3.41 (s) (together 2H), 6.35–6.45 (2H, m), 6.79 (1H, d), 8.15 (s) and 8.18 (s) (together 1H), m/z (API+): 177 (MH$^+$).

DESCRIPTION 14

2-(2-tert-Butyldimethylsilyloxyethyl)-7-nitro-1,2,3,4-tetrahydroisoquinoline

7-Nitro-tetrahydroisoquinoline (5.0 g; 28.0 mmol) was dissolved in DMF (150 ml). This solution was treated with (2-bromoethoxy)-tert-butyl-dimethylsilane (12.0 ml; 56.0 mmol), and stirred at 80° C. overnight. The mixture was cooled to room temperature and the solvent removed in vacuo. Purification by column chromatography through SiO$_2$, eluting with 50% diethyl ether/petroleum ether gave the title compound (4.2 g, 44%).

$^1$H NMR (250 MHz; CDCl$_3$) δ: 0.00 (6H, s), 0.83 (9H, s), 2.66 (2H, t, J=6 Hz), 2.79 (2H, t, J=6 Hz), 2.90 (2H, t, J=6 Hz), 3.71 (2H, s), 3.77 (2H, t, J=6 Hz), 7.16 (1H, d, J=9 Hz), 7.82 (1H, d, J=2 Hz), 7.89 (1H, dd, J=9, 2 Hz).

DESCRIPTION 15

7-Amino-2-(2-tert-butyldimethylsilyloxyethyl)-1,2,3,4-tetrahydroisoquinoline 2-(2-tert-Butyldimethylsilyloxyethyl) compound D14 (2.88 g; 8.57 mmol) and 10% Pd/C (0.5 g, 60% paste in water) in methanol (100 ml) was hydrogenated in a manner similar to that of Description 5 to give the title compound (2.62 g).

$^1$H NMR (250 MHz, CDCl$_3$) δ: 0.00 (6H, s), 0.83 (9H, s), 2.61 (2H, t, J=6 Hz), 2.71 (4H, s, overlapping signals), 3.55 (2H, s), 3.77 (2H, t, J=6 Hz), 6.27 (1H, d, J=2 Hz), 6.43 (1H, d, J=8 Hz), 6.80 (1H, d, J=8 Hz).

DESCRIPTION 16

2-(2-tert-Butyldimethylsilyloxyethyl)-1,2,3,4-tetrahydro-isoquinolin-7-yl)-3-bromo-4-ethoxybenzamide Triethylamine (0.112 ml; 0.81 mmol) and 3-bromo-4-ethoxybenzoyl chloride (193 mg; 0.73 mmol) were dissolved in dichloromethane (100 ml) with stirring. To this mixture was added the compound of D15 (204 mg; 0.67 mmol). The mixture was stirred overnight, and then evaporated in vacuo. The resultant residue was purified by chromatography on silica with 10% methanol:dichloromethane to give the title compound (123 mg; 35%).

$^1$H NMR (250 MHz; CDCl$_3$) δ: 0.0 (6H, s), 0.82 (9H, s), 1.42 (3H, t, J=7 Hz), 2.80 (2H, t, J=5 Hz), 2.91 (2H, t, J=5 Hz), 2.95 (2H, t, J=4 Hz), 3.81 (2H, s), 3.87 (2H, t, J=6 Hz), 4.08 (2H, q, J=7 Hz), 6.84 (1H, d, J=9 Hz), 7.00 (1H, d, J=8 Hz), 7.29 (2H, d, J=8 Hz), 7.33 (1H, s), 7.77 (1H, dd, J=9, 2 Hz), 8.00 (1H, d, J=2 Hz).

DESCRIPTION 17

7-Amino-2-(2-methoxyethyl)-1,2,3,4-tetrahydroisoquinoline $^1$H NMR (250 MHz; CDCl$_3$) δ: 2.74 (6H, m), 3.38 (3H, s), 3.60 (4H, m), 3.20–3.70 (2H, br), 6.37 (1H, s), 6.50 (1H, dd, J=8, 2 Hz), 6.88 (1H, d, J=8 Hz).

DESCRIPTION 18

5-Iodo-7-nitro-1,2,3,4-tetrahydroisoquinoline

The nitro compound of Description 3 (750 mg; 3.9 mmol) and N-iodosuccinimide (1.13 g) in triflic acid (5 ml) was stirred at 25° C. overnight. The mixture was poured cautiously into saturated NaHCO$_3$ and then extracted into ether (2×). The combined organic extracts were washed with aqueous sodium thiosulfate, dried (MgSO$_4$) and evaporation in vacuo gave a residue. Chromatography on Kieselgel 60 in 2% methanol-dichloromethane gave the title compound (650 mg).

DESCRIPTION 19

7-Amino-5-Iodo-1,2,3,4-tetrahydroisoquinoline

A solution of the nitro compound D18 (650 mg, 2.14 mmol) in ethanol (20 ml) at 50° C. was treated with a solution of tin (II) chloride (1.42 g) in c. HCl (3 ml). The resultant yellow solution was basified with 10% aqueous sodium hydroxide and the product extracted into dichloromethane. Flash chromatography on Kieselgel 60 (5% methanol-dichloromethane) gave the title compound (428 mg; 73%).

DESCRIPTION 20

7-Amino-5-Iodo-2-(tert-butoxycarbonyl)-1,2,3,4-tetrahydroisoquinoline

The iodoamine D19 (580 mg, 2.12 mmol) in DMF (30 ml) was treated with DMAP (20 mg) and di-tert-butyl-dicarbonate (466 mg, 2.13 mmol) and the solution was stirred at room temperature overnight. The reaction mixture was evaporated to dryness in vacuo. Chromatography on Kieselgel 60 (2% methanol-dichloromethane) gave the title compound (745 mg; 94%).

DESCRIPTION 21

5,7-Dinitro-1,2,3,4-tetrahydroisoquinoline

5-Nitro-1,2,3,4-tetrahydroisoquinoline (1.0 g, 5.6 mmol) in conc. sulfuric acid (3 ml) was treated with conc. nitric acid (1 ml) and the mixture stirred at room temperature for 1 h. The mixture was cooled, basified with 40% aqueous NaOH and work-up with dichloromethane gave the title compound (1.14 g).

DESCRIPTION 22

5,7-Dinitro-2-methyl-1,2,3,4-tetrahydroisoquinoline

The amine D21 (1.8 g) in formic acid (5 ml) and paraformaldehyde (7 ml) were reacted in a similar manner to that of Description 2 to give the title compound (1.74 g, 91%).

$^1$H NMR (CDCl$_3$) δ: 2.51 (3H, s), 2.75 (2H, t), 3.27 (2H, t), 3.75 (2H, s), 8.16 (1H, d, J=2 Hz), 8.66 (1H, d, J=2 Hz); m/z (CI): 238.1 (MH$^+$; 100%).

DESCRIPTION 23

5-Amino-7-nitro-2-methyl-1,2,3,4-tetrahydroisoquinoline

The dinitro compound D22 (1.7 g) was reduced with tin(II)chloride (5.42 g) in a manner similar to that of Description 19 to give the title compound (0.6 g).

DESCRIPTION 24

5-Trifluoroacetylamino-7-nitro-2-methyl-1,2,3,4-tetrahydroisoquinoline

The amine D23 (0.5 g) in dichloromethane (10 ml) and triethylamine (1.5 eq) was treated with trifluoroacetic anhydride (1.1 eq) and the mixture stirred at 25° C. for 3 h. Work-up with dichloromethane followed by chromatography on Kieselgel 60 in 3% methanol:dichloromethane gave the title compound (0.7 g, 96%).

m/z (CI): 304 (MH$^+$; 80%).

DESCRIPTION 25

7-Amino-5-trifluoroacetylamino-2-methyl-1,2,3,4-tetrahydroisoquinoline

The nitro compound D24 (0.7 g, 2.28 mmol) in ethanol (20 ml) was hydrogenated over 10% Pd/C (70 mg). The catalyst was removed by filtration through Celite and evaporation in vacuo gave the title compound as a pale solid (0.6 g, 93%).

DESCRIPTION 26

5-Chloro-7-nitro-2-methyl-1,2,3,4-tetrahydroisoquinoline

The 5-amino compound D23 (1.6 g, 7.7 mmol) in 5MHCl (25 ml) at 0° C. was treated with a solution of sodium nitrite (0.55 g, 8.0 mmol) in water (3 ml) over 5 min. The cold solution was then added gradually to a solution of copper (I)chloride (1.0 g, 10 mmol) in 5MHCl (25 ml). The mixture was stirred at 25° C. for 30 min and then basified with 40% NaOH. Work-up with dichloromethane (300 ml) followed by flash chromatography on Kieselgel 60 (5% methanol:dichloromethane) gave the title compound (1.1 g, 62%) as a yellow solid.

$^1$H NMR (CDCl$_3$) δ: 2.32 (3H, s), 2.61 (2H, t), 2.79 (2H, t), 3.57 (2H, s), 7.96 (1H, d, J=2 Hz), 8.08 (1H, d, J=2 Hz).

DESCRIPTION 27

7-Amino-5-chloro-2-methyl-1,2,3,4-tetrahydroisoquinoline

The nitro D26 (0.80 g, 3.5 mmol) in ethanol (70 ml) and conc. HCl (7 ml) was heated to 50° C. and tin(II)chloride (2.66 g, 14 mmol) was added. The mixture was heated for 15 min and allowed to cool; work-up similar to that described in Description 19 gave the title compound as a yellow oil (0.48 g).

$^1$H NMR (CDCl$_3$) δ: 2.42 (3H, s), 2.64 (2H, m), 2.77 (2H, m), 3.45 (2H, d), 6.27 (1H, d, J=2 Hz), 6.59 (1H, d, J=2 Hz).

PREPARATION 1

3-Bromobenzyl TBMS Ether

To a solution of 3-bromobenzyl alcohol (5.00 g, 0.027 mole) in dichloromethane (30 ml) and Et$_3$N (4.2 ml, 0.03 mole) was added a 1M solution tert-butyldimethylsilyl chloride in dichloromethane (28.0 ml) dropwise. The mixture was allowed to stir at room temperature overnight, then water (30 ml) was added. The organic layer was washed with brine, dried (Na$_2$SO$_4$) and evaporated to give a red oil which was purified by flash chromatography on silica gel using 20% ether in hexane to give a colourless oil (8.0 g).

PREPARATION 2

3-Pivaloylbenzylalcohol TBDMS Ether n-Butylithium (2.80 ml, 7.0 mmol, 2.5M in hexane) was slowly added to a solution of Preparation 1 TBDMS ether (1.80 g, 6.0 mmol) in dry THF (10 ml) over 5 min at −78° C. The reaction mixture was maintained under argon at −78° C. for 1 h, and N,O-dimethylhydroxy pivaloyl amide (0.86 g, 6.60 mmol) in THF (2 ml) was added dropwise with stirring at −78° C. The resulting mixture was allowed to stir at −78° C. for 2.5 h, quenched with NH$_4$Cl solution and allowed to warm to room temperature. The mixture was extracted with ether (2×50 ml), the combined organics were dried (Na$_2$SO$_4$) and concentrated in vacuo to give the title compound as a colourless oil (1.75 g m/z (API+): 307 (MH$^+$; 8%).

PREPARATION 3

3-Pivaloylbenzylalcohol

The ether of Preparation 2 (1.47 g, 4.80 mmol) was dissolved in methanol (25 ml); conc. HCl (20 drops) was added and the whole allowed to stir at room temperature for 4 h. Saturated NaHCO$_3$ solution was added and the mixture extracted with ether (2×50 ml).

The organic layer was dried over sodium sulfate and evaporation in vacuo gave title compound as a colourless oil (0.80 g).

m/z (API+): 193 (MH$^+$; 17%).

PREPARATION 4

3-Pivaloylbenzoic acid

3-Pivaloylbenzyl alcohol (0.80 g, 4.16 mmol) was dissolved in dioxane (20 ml). A solution of KOH (0.35 g, 6.30 mmol) in water (5 ml) was added followed by KMnO$_4$ (145 g, 9.17 mmol). The mixture was stirred at room temperature over the weekend. The solution was filtered through Celite and extracted with ether. The aqueous phase was acidified with dil. HCl and extracted with ether (3×50 ml). The organic layer was dried over magnesium sulphate and concentrated in vacuo to afford the title compound as a white solid (0.80 g).

$^1$H NMR (250 MHz, CDCl$_3$) δ: 1.38 (9H, s), 7.55 (1H, t), 7.92 (1H, d, J=6.5 Hz), 8.20 (1H, d, J=6.5 Hz), 8.44 (1H, s).

PREPARATION 5

3-Trifluoroacetylbenzoic acid

The title compound was prepared from diethyl trifluoroacetamide and 3-bromobenzyl TBDMS ether using a method similar to that described in Preparations 1, 2, 3 and 4.

m/z (API−): 217 (M−H$^+$; 20%).

PREPARATION 6

Methyl 3-Chloro-4-iso-propoxybenzoate

Methyl 3-chloro-4-hydroxybenzoate (5 g, 26.8 mmol) in DMF (45 ml) was treated with potassium carbonate (7.41 g, 53.6 mmol), 2-iodopropane (3.85 ml, 40.2 mmol) and then stirred at 25° C. for 18 h. Work-up with ethyl acetate gave the title compound (6.1 g).

PREPARATION 7

3-Chloro-4-iso-propoxybenzoic acid

Methyl 3-chloro-4-iso-propoxybenzoate (5.5 g, 24.1 mmol) was hydrolysed using 1M NaOH (36 ml) in methanol (80 ml). Extraction and work-up with ethyl acetate gave the title compound (4.3 g).

$^1$H NMR (DMSO-D$_6$) δ: 1.33 (6H, d), 4.79 (1H, m), 7.24 (1H, d), 7.87 (2H, m).

PREPARATION 8

3-Bromo-4-ethoxybenzoic acid

The title compound was prepared from 4-ethoxybenzoic acid in a manner similar to that of Procedure 1.

$^1$H NMR (DMSO-D$_6$) δ: 1.45 (3H, t, J=7 Hz), 4.26 (2H, q, J=7 Hz), 7.26 (1H, d, J=9 Hz), 7.98 (1H, dd, J=2.9 Hz), 8.12 (1H, d, J=2 Hz).

PREPARATION 9

3-Bromo-4-ethylbenzoic acid

The title compound was prepared from 4-ethylbenzoic acid.

$^1$H NMR (DMSO-D$_6$) δ: 1.20 (3H, t, J=7 Hz), 2.78 (2H, q, J=7 Hz), 7.50 (1H, d, J=8 Hz), 7.90 (1H, dd, J=2, 8 Hz), 8.07 (1H, d, J=8 Hz.

PREPARATION 10

3-Cyano-4-iso-propylbenzoic acid

The title compound was prepared from 4-iso-propylbenzoic acid similar to that described in Procedure 5.

$^1$H NMR (DMSO-D$_6$) δ: 1.07 (6H, d, J=7 Hz), 3.13 (1H, m, overlapped), 7.48 (1H, d, J=7 Hz), 7.96 (1H, dd, J=2, 8 Hz)), 8.00 (1H, d, J=2 Hz).

PREPARATION 11

4-Methoxy-3-trifluoromethylbenzoic acid

The title compound was prepared from 3-bromo-4-methoxybenzoic acid and potassium trifluoroacetate in a manner similar to that of Procedures 3 and 4.

$^1$H NMR (DMSO-D$_6$) δ: 3.78 (3H, s), 7.18 (1H, d, J=9 Hz), 7.90 (1H, d, J=2 Hz), 8.00 (1H, dd, J=2, 9 Hz), 12.70–13.10 (1H, br, exchangeable).

PREPARATION 12

4-Methoxy-3-trifluoromethylbenzoyl chloride

The title compound was prepared from 4-methoxy-3-trifluoromethylbenzoic acid with oxalyl chloride and DMF in chloroform at room temperature [D. Levin, Chem. Br., 1977, 20] followed by evaporation in vacuo.

PREPARATION 13

Methyl 3-Bromo-4-iso-propoxybenzoate

Methyl 3-bromo-4-hydroxybenzoate (2.5 g, 10.8 mmol) in DMF (35 ml) was treated with potassium carbonate (3.0 g, 21.6 mmol), 2-iodopropane (2.76, 21.6 mmol) and then stirred at 25° C. for 48 h. Work-up with ethyl acetate gave the title compound (3.0 g).

$^1$H NMR (250 MHz, CDCl$_3$) δ: 1.41 (6H, d, J=7 Hz), 3.89 (3H, s), 4.66 (1H, m), 6.90 (1H, d, J=8 Hz), 7.93 (1H, dd, J=8, 2 Hz), 8.22 (1H, d, J=2 Hz).

PREPARATION 14

Methyl 3-Cyano-4-iso-propoxybenzoate

Methyl 3-bromo-4-iso-propoxybenzoate (2.0 g, 7.3 mmol) and copper(I)cyanide in N-methyl pyrrolidone (50 ml) were heated under vigorous reflux for 4 h. Work-up with ethyl acetate gave the title compound (1.0 g).

$^1$H NMR (250 MHz, CDCl$_3$) δ: 1.56 (6H, d, J=7 Hz), 4.05 (3H, s), 4.88 (1H, m), 7.13 (1H, d, J=8 Hz), 8.31 (1H, dd, J=8, 2 Hz), 8.38 (1H, d, J=2 Hz).

PREPARATION 15

Methyl 3,5 Dichloro-4-ethoxybenzoate

The title compound was prepared in 69% yield from methyl 3,5-dichloro-4-hydroxybenzoic acid and iodoethane in a manner similar to that of Preparation 6.

$^1$H NMR (250 MHz, CDCl$_3$) δ: 1.47 (3H, t, J=7 Hz), 3.91 (3H, s), 4.16 (2H, q, J=7 Hz), 7.96 (2H, s).

PREPARATION 16

3-Methanesulfonyl-4-iso-propylbenzoic acid

3-Chlorosulfonyl-4-iso-propylbenzoic acid (2.62 g, 10 mmol) [made from 4-iso-propyl benzoic acid in a manner similar to that described in Procedures 7 and 8] was added slowly to a slurry of NaHCO$_3$ (2.52 g, 30 mmol) and Na$_2$SO$_3$ (1.26 g 10 mmol) in water (9 ml) at 75° C. The mixture was stirred for 1 h and then treated with bromoacetic acid (2.08 g, 15 mmol) and NaOH (0.60 g, 15 mmol). The temperature was raised to 105° C. and the mixture heated at reflux for 24 h. The mixture was cooled, acidified to pH 1 and the resultant precipitate collected, washed and dried to give the title compound (1.43 g, 59%).

$^1$H NMR (250 MHz, acetone-D$_6$) δ: 1.24 (6H, d, J=7 Hz), 3.13 (3H, s), 3.88 (1H, m), 7.72 (1H, d, J=7 Hz), 8.15 (1H, dd, J=7 Hz), 8.52 (1H, d, J=2 Hz).

PREPARATION 17

4-Methyl-3-methanesulfonylbenzoic acid

Prepared in 30% overall yield in a manner similar to that of Preparation 16.

$^1$H NMR (250 MHz, acetone-D$_6$) δ: 2.57 (3H, s), 2.99 (3H, s), 7.39 (1H, d, J=7 Hz), 7.97 (1H, dd, J=7, 2 Hz), 8.39 (1H, d, J=2 Hz).

PREPARATION 18

4-Ethyl-3-methanesulfonylbenzoic acid

Prepared in 44% overall yield in a manner similar to that of Preparation 16.

$^1$H NMR (250 MHz, acetone-D$_6$) δ: 1.22 (3H, t, J=7 Hz), (3H, s), 3.05 (2H, q, J=7 Hz), 3.12 (3H, s), 7.57 (1H, d, J=7 Hz), 8.13 (1H, dd, J=7, 2 Hz), 8.51 (1H, d, J=2 Hz).

PREPARATION 19

3-Methanesulfonyl-4-methoxybenzoic acid

Prepared in 20% overall yield in a manner similar to that of Preparation 16.

$^1$H NMR (250 MHz, acetone-D$_6$) δ: 3.00 (3H, s), 3.89 (3H, s), 7.17 (1H, d, J=7 Hz), 8.06 (1H, dd, J=7, 2 Hz), 8.31 (1H, d, J=2 Hz).

PREPARATION 20

4-Ethoxy-3-methanesulfonylbenzoic acid

Prepared in 20% overall yield in a manner similar to that of Preparation 16.

$^1$H NMR (250 MHz, acetone-D$_6$) δ: 1.44 (3H, t, J=7 Hz), (3H, s), 3.30 (3H, s), 4.35 (2H, q, J=7 Hz), 7.40 (1H, d, J=7 Hz), 8.20 (1H, dd, J=7.2 Hz), 8.37 (1H, d, J=2 Hz).

PREPARATION 21

3-Chloro-4-ethoxybenzoic acid $^1$H NMR (DMSO-D$_6$) δ: 1.39 (3H, t, J=7 Hz), 4.20 (2H, q, J=7 Hz), 7.22 (1H, d, J=7 Hz), 7.87 (2H, m).

PREPARATION 22

4-iso-Propyloxy-3-trifluoromethylbenzoic acid

Methyl 3-bromo-4-iso-propyloxybenzoate (828 mg; 3.03 mmol) in DMF (25 ml) was treated with potassium trifluoromethylate (922 mg; 6.06 mmol), copper (I) iodide (1.15 g; 6.06 mmol) and toluene (50 ml). The resulting mixture was heated at reflux for 1.5 h (Dean and Stark with removal of ca 50 ml of distillate) followed by reflux for 18 h then cooled. The mixture was poured into Et$_2$O (100 ml) and H$_2$O (100 ml). The two-phase mixture was stirred at room temperature for 0.5 h then filtered through Celite. The two phases were separated, the aq. phase further extracted with Et$_2$O (50 ml) and the organic extracts combined, washed with saturated, aq. Na$_2$S$_2$O$_3$. H$_2$O, saturated brine, dried (MgSO$_4$) and evaporated in vacuo to give a brown oil. This was dissolved in MeOH (ca 20 ml) and treated with 2M NaOH (2 ml; 4 mmol) and the resulting solution heated at reflux for 3 h. The volatiles were removed in vacuo and the residue partitioned between EtOAc and H$_2$O. The phases were separated, the aq. phase acidified to pH1 with 2M HCl in the presence of EtOAc and the phases separated. The aq. phase was further extracted with EtOAc, the extracts combined, washed with H$_2$O, saturated brine, dried (MgSO$_4$) and evaporated to dryness in vacuo to give the title compound as a white solid (671 mg; 89%).

$^1$H NMR (250 MHz; (CD$_3$)$_2$CO) δ: 1.02 (6H, d, J=6 Hz), 4.53–4.63 (1H, m), 7.01 (1H, d, J=9 Hz), 7.85–7.88 (2H, m); m/z, (API): 205.0 [M–Pr$^1$].

PREPARATION 23

4-Ethyl-3-trifluoromethylbenzoic acid

Prepared as described in Preparation 22 from methyl 4-ethyl-3-bromobenzoate (1.10 g; 4.52 mmol) and isolated as a white solid (923 mg; 93%).

¹H NMR (250 MHz; (CD₃)₂CO) δ: 0.98 (3H, t, J=7 Hz), 2.60 (2H, q, J=7 Hz), 7.36 (1H, d, J=8 Hz), 7.89 and 7.93 (1H, m), 7.96 (1H, br s); m/z (API): 217.1 [M−H].

PREPARATION 24

4-n-Propyloxy-3-trifluoromethylbenzoic acid

Prepared as described in Preparation 22 from methyl 3-bromo-4-n-propyloxybenzoate (1.43 g; 5.23 mmol) and isolated as a white solid (1.18 g; 91%).

¹H NMR (250 MHz; (CD₃)₂SO) δ: 1.09 (3H, t, J=7 Hz), 1.79–1.93 (2H, m), 4.26 (2H, t, J=6 Hz), 7.45 (1H, d, J=9 Hz), 8.19 (1H, d, J=2 Hz), 8.25 and 8.28 (1H, dd, J=9, 2 Hz); m/z (API): 203.1 [M−CO₂H].

PREPARATION 25

4-t-Butyl-3-trifluoromethylbenzoic acid

Prepared as described in Preparation 22 from methyl 3-bromo-4-t-butylbenzoate (2.46 g; 9.1 mmol) and isolated as a white solid (1.55 g; 69%).

¹H NMR (250 MHz; (CD₃)₂SO) δ: 1.42 (9H, s), 7.86–7.90 (1H, m), 8.09–8.13 (1H, m), 8.23 (1H, d, J=2 Hz); m/z (API): 245.1 [M−H].

PREPARATION 26

4-Oxochroman-6-carboxylic acid 3-(4-Carboxyphenoxy)propionic acid (2.5 g) [prepared according to the procedure of J. Lichtenberger and R. Geyer. Bull. Soc. Chim. Fr., 1963 275] in conc. sulfuric acid (20 ml) was heated to 100° C. for 4 h and then poured onto crushed ice. The resultant precipitate was filtered and dried in vacuo to give the title compound (1.6 g).

¹H NMR (DMSO-D₆) δ: 2.99 (2H, t, J=7 Hz), 4.77 (2H, t, J=7 Hz), 7.28 (1H, d, J=8 Hz), 8.21 (1H, dd, J=8, 2 Hz), 8.46 (1H, d, J=2 Hz).

PREPARATION 27

3-Bromo-4-iso-propoxybenzoic acid

The title compound was prepared using a method similar to that of Preparation 7.

¹H NMR (DMSO-D₆) δ: 1.29 (6H, d, J=7 Hz), 4.77 (1H, sep, J=7 Hz), 7.20 (1H, d, J=8 Hz), 7.87 (1H, dd, J=8, 2 Hz), 8.02 (1H, d, J=2 Hz), 12.92 (1H, brs).

PREPARATION 28

4-Azidobenzoic acid

To a solution of 4-aminobenzoic acid (2.00 g, 14.00 mmol) in trifluoroacetic acid (10 ml) at 5° C., was added sodium nitrite (3.50 g) portionwise, and the mixture allowed to stir for 30 min. Sodium azide (3.79 g,) was then added portionwise and the mixture stirred for a further 30 min at 0° C. The mixture was diluted with water, and a white solid precipitated. The solid was filtered, washed with cold water and dried, to afford the title compound (1.66 g, 73%).

PROCEDURE 1

5-Bromo-2,4-dimethoxybenzoic acid

To a solution of 2,4-dimethoxybenzoic acid (4.0 g, 0.022 mol) in chloroform (60 ml) was added bromine (1.13 ml, 0.022 mol) in chloroform (20 ml) dropwise. After stirring overnight at room temperature the precipitate was filtered off and dried to afford the title compound as a white solid (2.87 g).

PROCEDURE 2

5-Bromo-4-iso-propyl-2-methoxybenzoic acid

To a solution of 2-methoxy-4-iso-propyl benzoic acid (7.0 g, 36.0 mmol) in chloroform (100 ml) was added bromine (1.86 ml) in chloroform (20 ml) dropwise. The reaction was stirred at room temperature overnight. Evaporation in vacuo afforded an oil (9.27 g).

m/z (CI): 275, 273 (MH⁺; 70%).

PROCEDURE 3

Methyl 5-bromo-4-iso-propyl-2-methoxy benzoate

5-Bromo-4-iso-propyl-2-methoxybenzoic acid (9.268 g 34.0 mmol) was dissolved in methanol (250 ml) and conc. H₂SO₄ (2 ml) added. The mixture was refluxed for 5 h and concentrated in vacuo. Residual material was taken up into ethyl acetate and water, and the organic layer, dried (MgSO₄). Concentration in vacuo afforded an oil, which was purified by Biotage Column Chromatography on silica gel using 10% ether in hexane to give an oil (5.5 g).

PROCEDURE 4

2,4-Dimethoxy-5-trifluoromethylbenzoic acid 2,4-Dimethoxy-5-bromobenzoic acid methyl ester (1.5 g; 5.4 mmol) in DMF (25 ml) and toluene (8 ml) under argon was treated with potassium trifluoroacetate (1.53 g; 10.1 mmol) and copper (I) iodide (2.1 g, 10.9 mmol). The mixture was heated to 170° C. with removal of water (Dean/Stark), and then at 155° C. overnight. The mixture was allowed to cool, poured into ether and water and filtered through Kieselguhr. The organic layer was dried (Na₂SO₄) and concentrated in vacuo to give a brown solid. Chromatography on Kieselgel 60 with 1:1 ether/petrol gave a solid (1.03 g) which was hydrolysed in 1:1 methanolic:aqueous NaOH (50 ml) at 50° C. Work-up gave the title compound as a white solid (1 g).

PROCEDURE 5a

Methyl 2-methoxy-5-cyano-4-iso-propylbenzoate

Copper (I) cyanide (550 mg, 6 mmol) was added to a solution of methyl 2-methoxy-5-bromo-4-iso-propylbenzoate (861 mg) in N-methyl-2-pyrrolidinone (30 ml). The mixture was stirred under argon and boiled under reflux for 4 h. The mixture was cooled, poured into excess ice/water and ethyl acetate and filtered. The organic phase was separated, washed with water, brine and dried(MgSO₄). Evaporation gave a crude brown solid which was purified by chromatography on silica gel eluting with ethyl acetate/n-hexane (1:4). The product was obtained as a white solid (523 mg).

¹H NMR (250 MHz, CDCl₃) δ: 1.33 (6H, d, J=7 Hz), 3.38 (1H, sep, J=7 Hz), 3.89 (3H, s), 3.98 (3H, s), 6.91 (1H, s), 8.08 (1H, s); m/z (API⁺): 234 (MH⁺, 30%).

PROCEDURE 5b

2-Methoxy-5-cyano-4-iso-propylbenzoic acid

2N NaOH (1.25 ml) was added to a solution of the methyl ester P5a (490 mg) in methanol (10 ml). The solution was stirred overnight at room temperature. The solution was then diluted with water, concentrated in vacuo and washed with ethyl acetate. The aqueous phase was then acidified with 2N HCl and extracted with ethyl acetate. The extract was washed with brine, dried (MgSO$_4$) and evaporated to dryness giving the product as a white solid (418 mg).

$^1$H NMR (250 MHz, CDCl$_3$) δ: 1.35 (6H, d, J=7 Hz), 3.43 (1H, sep, J=7 Hz), 4.14 (3H, s), 7.00 (1H, s), 8.41 (1H, s); m/z (API$^+$): 220 (MH$^+$, 100%).

PROCEDURE 6a

Ethyl 2-ethoxy-4-iso-propyl-5-cyanobenzoate

Ethyl 2-ethoxy-4-iso-propyl-5-bromobenzoate (1.2 g, 3.8 mmol) was treated with copper (I) cyanide (682 mg, 7.6 mmol) in N-methyl-2-pyrrolidinone (40 ml) as described in Procedure 5 to give the title compound as an oil (400 mg).

$^1$H NMR (250 MHz, CDCl$_3$) δ: 1.12 (6H, d, J=7 Hz), 1.30 (3H, t, J=7 Hz), 1.84 (3H, t, J=7 Hz), 3.17 (1H, sep, J=7 Hz), 3.99 (2H, q, J=9 Hz), 4.16 (2H, q, J=7 Hz), 6.69 (1H, s), 7.86 (1H, s); m/z (API$^+$): 262 (MH$^+$, 100%).

PROCEDURE 6b

2-Ethoxy-4-iso-propyl-5-cyanobenzoic acid

The ester P6a (370 mg, 1.41 mmol) was dissolved in methanol (5 ml) and over a 24 h period 1N NaOH (2.1 ml, 2.1 mmol) was added. The solution was concentrated under vacuum, diluted with water and washed with ethyl acetate. The aqueous phase was acidified with 2N HCl and extracted with ethyl acetate. The extract was washed with brine, dried (MgSO$_4$) and evaporated to give the title acid (306 mg).

$^1$H NMR (250 MHz CDCl$_3$) δ: 1.39 (3H, d, J=7 Hz), 1.66 (3H, t, J=7 Hz), 3.47 (1H, sep, J=7 Hz), 4.46 (2H, q, J=7 Hz), 7.03 (1H, s), 8.47 (1H, s); m/z (API$^+$): 234 (MH$^+$, 100%).

PROCEDURE 7

4-Ethoxy-2-methoxy-5-methylsulfonylbenzoic acid

4-Ethoxy-2-methoxy-5-chlorosulfonyl benzoic acid was prepared in 49% yield using the procedure of M. W. Harrold et al., J. Med. Chem., 1989, 32 874. This was used according to the method of R. W. Brown, J. Org. Chem., 1991, 56, 4974, to the title compound in 19% yield.

$^1$H NMR (DMSO-D$_6$) δ: 1.30 (3H, t), 3.10 (3H, s), 3.83 (3H, s), 4.24 (2H, q), 6.73 (1H, s), 8.07 (1H, s).

PROCEDURE 8

4-iso-Propyl-2-methoxy-5-methylsulfonylbenzoic acid

This was prepared in a similar manner to the procedure of C. Hansch, B. Schmidhalter, F. Reiter, W. Saltonstall, J. Org. Chem., 1956, 21, 265 to afford the intermediate 5-chlorosulfonyl-4-isopropyl-2-methoxybenzoic acid which was converted into the title compound using the method of Procedure 7.

$^1$H NMR (DMSO-D$_6$) δ: 1.30 (6H, d), 3.21 (3H, s), 3.80 (1H, m), 3.94 (3H, s), 7.26 (1H, s), 8.19 (1H, s).

EXAMPLE 1

N-(1,2,3,4-Tetrahydroisoquinolin-7-yl)-5-chlorothiophene-2-carboxamide, monotrifluoroacetate The N-boc amine D7 (0.48 g; 1.22 mmol) in dichloromethane (25 ml) containing trifluoroacetic acid (2 ml) was kept at 25° C. for 18 h. Evaporation in vacuo followed by crystallisation of the residue from ethyl acetate-ether gave the title compound as off-white crystals (0.46 g; 92%), m.p. 153–5° C.

$^1$H NMR (400 MHz, DMSO-d$^6$) δ: 2.96 (2H, t), 3.38 (2H, t), 4.29 (2H, s), 7.23 (1H, d), 7.28 (1H, d, ABq), 7.51 (1H, dd), 7.63 (1H, d), 7.90 (1H, d, ABq), 9.01 (2H, br, s), 10.33 (1H, s); m/z (CI): 293 (MH$^+$; 100%).

EXAMPLE 2

N-(2-Methyl-tetrahydroisoquinolin-7-yl)-5-chlorothiophene-2-carboxamide

The compound of Example 1 (200 mg; 0.5 mmol), 98% formic acid (0.4 ml) and aqueous formaldehyde (0.6 ml) were treated according to the procedure of Description 4. Chromatography on Kieselgel 60 in methanol-ethyl acetate followed by crystallisation from ethyl acetate-ether gave the title compound as an off-white powder, m.p. 138–40° C.

$^1$H NMR (250 MHz, CDCl$_3$) δ: 2.46 (3H, s), 2.69 (2H, t), 2.89 (2H, t), 3.54 (2H, s), 6.93 and 7.37 (2H, ABq), 7.07 (1H, d), 7.25 (1H, dd), 7.34 (1H, d), 7.63 (1H, br, s); m/z (CI): 307 (MH$^+$; 100%).

EXAMPLE 3

N-(2-Methyl-1,2,3,4-tetrahydroisoquinolin-7-yl)benzamide

The N-methyl amine D5 in dichloromethane (25 ml) containing triethylamine (0.5 ml) was treated with benzoyl chloride and the mixture kept at 25° C. for 18 h. Normal work-up gave the product which was chromatographed on Kieselgel 60 by gradient elution in ethyl acetate:hexane. Combination of appropriate fractions gave the title compound.

$^1$H NMR (250 MHz, CDCl$_3$) δ: 2.46 (3H, s), 2.69 (2H, t), 2.91 (2H, t), 3.58 (2H, s), 7.10 (1H, d), 7.30 (1H, dd), 7.40–7.60 (4H, overlapping m), 7.75 (1H, br s), 7.87 (2H, m).

The following Examples were made using procedures similar to the methods described earlier.

EXAMPLE 4

N-(2-Methyl-1,2,3,4-tetrahydroisoquinolin-7-yl)-3-chlorobenzamide $^1$H NMR (250 MHz, CDCl$_3$) δ: 2.46 (3H, s), 2.68 (2H, t), 2.90 (2H, t), 3.57 (2H, s), 7.10 (1H, d), 7.29 (1H, dd, overlapping with CHCl$_3$), 7.39 (1H, s), 7.42 (1H, d), 7.52 (1H, m), 7.73 (1H, m), 7.83 (2H, m).

EXAMPLE 5

N-(2-Methyl-1,2,3,4-tetrahydroisoquinolin-7-yl)-4-t-butylbenzamide $^1$H NMR (250 MHz, CDCl$_3$) δ: 1.34 (9H, s), 2.44 (3H, s), 2.68 (2H, t), 2.89 (2H, t), 3.55 (2H, s), 7.07 (1H, d), 7.29 (1H, dd overlapping with CHCl$_3$ signal), 7.38–7.53 (3H, m, overlapping signals), 7.75–7.90 (3H, m, overlapping signals).

EXAMPLE 6

N-(2-Methyl-1,2,3,4-tetrahydroisoquinolin-7-yl)-4-iso-propoxybenzamide $^1$H NMR (250 MHz, CDCl$_3$) δ: 1.38 (6H, d), 2.46 (3H, s), 2.69 (2H, t), 2.90 (2H, t), 3.58 (2H, s), 4.64 (1H, septet), 6.94

(2H, m), 7.09 (1H, d), 7.23–7.34 (1H, m, overlapping CHCl$_3$), 7.42 (1H, s), 7.70 (1H, br s), 7.81 (2H, m); m/z (CI): 325 (MH$^+$, 100%).

EXAMPLE 7

N-(2-Methyl-1,2,3,4-tetrahydroisoquinolin-7-yl)-4-phenoxybenzamide $^1$H NMR (250 MHz, CDCl$_3$) δ: 2.46 (3H, s), 2.69 (2H, t), 2.91 (2H, t), 3.59 (2H, s), 7.00–7.50 (10H, overlapping m), 7.72 (1H, br s), 7.83 (2H, m).

EXAMPLE 8

N-(2-Methyl-1,2,3,4-tetrahydroisoquinolin-7-yl)-4-nitrobenzamide $^1$H NMR (CDCl$_3$) δ: 2.45 (3H, s), 2.70 (2H, m), 2.90 (2H, m), 3.60 (2H, s), 7.10 (2H, dd), 7.25 (1H, dd), 7.40 (1H, d), 8.00 (2H, dd), 8.35 (2H, dd), 7.80 (1H, s). m/z (CI): 312 (MH$^+$, 70%).

EXAMPLE 9

N-(2-Methyl-1,2,3,4-tetrahydroisoquinolin-7-yl)-4-phenylbenzamide $^1$H NMR (CDCl$_3$) δ: 2.45 (3H, s), 2.70 (2H, m), 2.90 (2H, m), 3.60 (2H, s), 6.30 (1H, d), 6.50 (1H, dd), 6.90 (1H, dd), 7.10 (1H, d), 7.40 (2H, m), 7.60 (1H, dd), 7.70 (1H, dd), 7.80 (1H, s), 7.90 (1H, d), 8.05 (1H, s); m/z (CI): 343 (MH$^+$; 90%).

EXAMPLE 10

N-(2-Methyl-1,2,3,4-tetrahydroisoquinolin-7-yl)-3-methylbenzamide $^1$H NMR (CDCl$_3$) δ: 2.43 (3H, s), 2.47 (3H, s), 2.70 (2H, t), 2.90 (2H, t), 3.60 (2H, s), 7.05 (1H, dd), 7.30 (1H, m), 7.35 (2H, m), 7.45 (1H, s), 7.65 (3H, m). m/z (CI): 281 (MH$^+$; 90%).

EXAMPLE 11

N-(2-Methyl-1,2,3,4-tetrahydroisoquinolin-7-yl)-3-fluorobenzamide $^1$H NMR (CDCl$_3$) δ: 2.50 (3H, s), 2.75 (2H, t), 2.90 (2H, t), 3.65 (2H, s), 7.10 (1H, dd), 7.28 (2H, m), 7.40 (2H, m), 7.60 (2H, m), 7.75 (1H, s); m/z (CI): 285 (MH$^+$; 100%).

EXAMPLE 12

N-(2-Methyl-1,2,3,4-tetrahydroisoquinolin-7-yl)-3-cyanobenzamide $^1$H NMR (CDCl$_3$) δ: 2.47 (3H, s), 2.70 (2H, t), 2.90 (2H, t), 3.60 (2H, s), 7.12 (1H, dd), 7.30 (1H, m), 7.40 (1H, s), 7.65 (1H, dt), 7.80 (2H, m), 8.10 (1H, d), 8.15 (1H, s). m/z (CI): 292 (MH$^+$).

EXAMPLE 13

N-(2-Methyl-1,2,3,4-tetrahydroisoquinolin-7-yl)-3,4-dichlorobenzamide $^1$H NMR (CDCl$_3$): 2.50 (3H, s), 2.80 (2H, t), 2.90 (2H, t), 3.70 (2H, s), 7.10 (1H, d), 7.30 (1H, dd), 7.40 (1H, s), 7.55 (1H, d), 7.70 (1H, dd), 8.00 (2H, m). m/z (CI): 335 (MH$^+$).

EXAMPLE 14

N-(2-Methyl-1,2,3,4-tetrahydroisoquinolin-7-yl)-4-iodobenzamide $^1$H NMR (CDCl$_3$) δ: 2.47 (3H, s), 2.71 (2H, t), 2.89 (2H, t), 3.58 (2H, s), 7.10 (1H, d), 7.30 (1H, m), 7.43 (1H, s), 7.60 and 7.85 (4H, ABq), 7.82 (1H, s). m/z (CI): 393 (MH$^+$; 100%).

EXAMPLE 15

N-2-Methyl-1,2,3,4-tetrahydroisoquinolin-7-yl)-4-bromobenzamide $^1$H NMR (CDCl$_3$) δ: 2.47 (3H, s), 2.71 (2H, t), 2.89 (2H, t), 3.60 (2H, s), 7.10 (1H, d), 7.30 (1H, m), 7.43 (1H, s), 7.64 and 7.74 (4H, ABq), 7.70 (1H, s). m/z (CI): 347, 345 (MH$^+$; 100%).

EXAMPLE 16

N-(2-Methyl-1,2,3,4-tetrahydroisoquinolin-7-yl)-4-methylbenzamide $^1$H NMR (CDCl$_3$) δ: 2.44 (3H, s), 2.48 (3H, s), 2.75 (2H, t), 2.90 (2H, t), 3.63 (2H, s), 7.10 (1H, d), 7.28 and 7.78 (4H, ABq), 7.30 (1H, m), 7.44 (1H, s), 7.74 (1H, m). m/z (CI): 281.2 (MH$^+$; 100%).

EXAMPLE 17

N-(2-Methyl-1,2,3,4-tetrahydroisoquinolin-7-yl)-3-nitrobenzamide $^1$H NMR (CDCl$_3$) δ: 2.48 (3H, s), 2.71 (2H, t), 2.92 (2H, t), 3.61 (2H, s), 7.13 (1H, d), 7.34 (1H, dd), 7.42 (1H, s), 7.71 (1H, t), 8.00 (1H, d), 8.26 (1H, d), 8.40 (1H, d), 8.70 (1H, t); m/z (CI): 312.1 (MH$^+$; 100%).

EXAMPLE 18

N-(2-Methyl-1,2,3,4-tetrahydroisoquinolin-7-yl)-4-ethoxybenzamide $^1$H NMR (CDCl$_3$) δ: 1.46 (3H, m), 2.47 (3H, s), 2.71 (2H, t), 2.90 (2H, t), 3.61 (2H, s), 4.11 (2H, m), 7.14 (1H, d), 7.30 (1H, m), 7.49 (1H, s), 7.68 (1H, s), 7.82 (2H, d), 8.10 (3H, m); m/z (CI): 311.2 (MH$^+$; 100%).

EXAMPLE 19

N-(2-Methyl-1,2,3,4-tetrahydroisoquinolin-7-yl)-4-n-butylbenzamide $^1$H NMR (CDCl$_3$) δ: 0.93 (3H, t), 1.25–1.48 (2H, m), 1.52–1.70 (2H, m), 2.51 (3H, s), 2.66 (2H, m), 2.80 (2H, t), 2.95 (2H, t), 3.69 (2H, s), 7.12 (1H, d), 7.20 (1H, d), 7.29 (2H, d), 7.32 (1H, m), 7.47 (1H, s), 7.78 (2H, d), 7.93 (1H, d); m/z (CI): 323.2 (MH$^+$; 100%).

EXAMPLE 20

N-(2-Methyl-1,2,3,4-tetrahydroisoquinolin-7-yl)-2-acetoxybenzamide $^1$H NMR (CDCl$_3$) δ: 2.33 (3H, s), 2.48 (3H, s), 2.71 (2H, t), 2.91 (2H, t), 3.61 (2H, s), 7.10 (1H, d), 7.16 (1H, d), 7.23 (1H, m), 7.32–7.45 (2H, m), 7.52 (1H, t), 7.83 (1H, d), 7.94 (1H, s); m/z (CI): 325.2 (MH$^+$; 100%).

EXAMPLE 21

N-(2-Methyl-1,2,3,4-tetrahydroisoquinolin-7-yl)-3-trifluoromethylbenzamide $^1$H NMR (CDCl$_3$) δ: 2.48 (3H, s), 2.73 (2H, t), 2.92 (2H, t), 3.62 (2H, s), 7.11 (1H, d), 7.32 (1H, d), 7.42 (1H, s), 7.63 (1H, t), 7.75–7.91 (2H, m), 8.07 (1H, t), 8.12 (1H, s). m/z (CI): 335.1 (MH$^+$; 100%).

EXAMPLE 22

N-(2-Methyl-1,2,3,4-tetrahydroisoquinolin-7-yl)-2,4-difluorobenzamide $^1$H NMR (CDCl$_3$) δ: 2.47 (3H, s), 2.71 (2H, t), 2.92 (2H, t), 3.61 (2H, s), 6.95 (1H, m), 7.00–7.18 (2H, m), 7.32 (1H, dd), 7.44 (1H, s), 8.14–8.36 (2H, m). m/z (CI): 303.1 (MH$^+$; 100%).

EXAMPLE 23

N-(2-Methyl-1,2,3,4-tetrahydroisoquinolin-7-yl)-3,4-dimethoxybenzamide m/z (CI): 327.2 (MH+; 100%).

EXAMPLE 24

N-(2-Methyl-1,2,3,4-tetrahydroisoquinolin-7-yl)-2-fluoro-4-trifluoromethylbenzamide $^1$H NMR (CDCl$_3$) δ: 2.47 (3H, s), 2.70 (2H, t), 2.92 (2H, t), 3.61 (2H, s), 7.11 (1H, d), 7.35 (1H, dd), 7.45 (2H, s), 7.50 (1H, s), 7.59 (1H, d), 8.20–8.40 (2H, br m). m/z (CI): 353.1 (MH+; 100%).

EXAMPLE 25

N-(2-Methyl-1,2,3,4-tetrahydroisoquinolin-7-yl)-4-chloro-3-nitrobenzamide $^1$H NMR (CDCl$_3$) δ: 2.48 (3H, s), 2.72 (2H, t), 2.94 (2H, t), 3.60 (2H, s), 7.10 (1H, d), 7.32 (1H, d), 7.38 (1H, s), 7.67 (1H, d), 7.95–8.13 (2H, br m), 8.38 (1H, d). m/z (CI): 348 (MH+; 33%), 346.1 (MH+; 100%).

EXAMPLE 26

N-(2-Methyl-1,2,3,4-tetrahydroisoquinolin-7-yl)-3,5-di-trifluoromethylbenzamide $^1$H NMR (CDCl$_3$) δ: 2.52 (3H, s), 2.78 (2H, t), 2.94 (2H, t), 3.66 (2H, s), 7.14 (1H, d), 7.36 (1H, d), 7.42 (1H, s), 7.94 (1H, m), 8.04 (1H, s), 8.32 (2H, s). m/z (CI): 403.1 (MH+; 100%).

EXAMPLE 27

N-(2-Methyl-1,2,3,4-tetrahydroisoquinolin-7-yl)-2,4-dichloro-5-fluorobenzamide $^1$H NMR (CDCl$_3$) δ: 2.47 (3H, s), 2.70 (2H, t), 2.91 (2H, t), 3.60 (2H, s), 7.11 (1H, d), 7.25 (1H, d), 7.38 (1H, s), 7.52 (1H, dd), 7.62 (1H, dd), 7.90 (1H, brs). m/z (CI): 353.0 (MH+; 100%).

EXAMPLE 28

N-(2-Methyl-1,2,3,4-tetrahydroisoquinolin-7-yl)-3-fluoro-5-trifluoromethylbenzamide $^1$H NMR (CDCl$_3$) δ: 2.49 (3H, s), 2.73 (2H, t), 2.91 (2H, t), 3.62 (2H, s), 7.13 (1H, d), 7.32 (1H, dd), 7.40 (1H, s), 7.50 (1H, d), 7.80 (1H, m), 7.90 (1H, s), 8.02 (1H, s). m/z (CI): 353.1 (MH+; 100%).

EXAMPLE 29

N-(2-Methyl-1,2,3,4-tetrahydroisoquinolin-7-yl)-3-bromo-4-methoxybenzamide $^1$H NMR (CDCl$_3$) δ: 2.47 (3H, s), 2.71 (2H, t), 2.91 (2H, t), 3.60 (2H, s), 3.97 (3H, s), 6.96 (1H, d), 7.10 (1H, d), 7.29 (1H, m), 7.40 (1H, s), 7.67 (1H, s), 7.84 (1H, dd), 8.02 (1H, s), 8.05 (1H, d); m/z (CI): 377, 375 (MH+; 30%).

EXAMPLE 30

N-(2-Methyl-1,2,3,4-tetrahydroisoquinolin-7-yl)-3,4,5-trimethoxybenzamide $^1$H NMR (CDCl$_3$) δ: 2.42 (3H, s), 2.66 (2H, t), 2.88 (2H, t), 3.55 (2H, 5), 3.83 (3H, s), 3.86 (6H, s), 7.00 (1H, s), 7.05 (1H, d), 7.19 (1H, s), 7.26 (1H, d), 7.34 (1H, s), 7.68 (1H, s), 7.94 (1H, s); m/z (CI): 357.2 (MH+; 100%).

EXAMPLE 31

N-(2-Methyl-1,2,3,4-tetrahydroisoquinolin-7-yl)-4-trifluoromethoxybenzamide $^1$H NMR (CDCl$_3$) δ: 2.47 (3H, s), 2.70 (2H, t), 2.91 (2H, t), 3.60 (2H, s), 7.10 (1H, d), 7.25 (1H, m), 7.32 (2H, d), 7.40 (1H, s), 7.74 (1H, s), 7.90 (2H, d); m/z (CI): 351.1 (MH+; 100%).

EXAMPLE 32

N-(2-Methyl-1,2,3,4-tetrahydroisoquinolin-7-yl)-3-pivaloylbenzamide, hydrochloride The acid of Preparation 5 (200 mg, 1.0 mmol) and oxalyl chloride (140 mg, 1.1 mmol) in dichloromethane (10 ml) containing DMF (5 drops) was stirred at 25° C. for 1 h and then evaporated to dryness in vacuo. The residue in dichloromethane was treated with the amine D5 (162 mg, 1.0 mmol) and kept at 25° C. overnight. Work-up similar to that of Example 2 gave the title compound (110 mg), m.p. 197–201° C. (from methanol:ether).

$^1$H NMR (free base; 250 MHz; CDCl$_3$) δ: 1.38 (9H, s), 2.45 (3H, s), 2.68 (2H, t), 2.89 (2H, t), 3.55 (2H, s), 7.08 (1H, d), 7.30 (1H, d), 7.40 (1H, s), 7.49 (1H, t), 7.83 (1H, d), 7.95 (1H, d), 8.08 (1H, s), 8.14 (1H, s); m/z (CI): 351.2 (MH+; 100%).

EXAMPLE 33

N-(2-Methyl-1,2,3,4-tetrahydroisoquinolin-7-yl)-3-bromo-4-iso-propoxybenzamide $^1$H NMR (CDCl$_3$) δ: 1.42 (6H, d, J=6 Hz), 2.47 (3H, s), 2.71 (2H, t, J=6 Hz), 2.91 (2H, t, J=6 Hz), 3.60 (2H, s), 4.67 (1H, dt, J=6 Hz), 6.96 (1H, d, J=9 Hz), 7.10 (1H, d, J=8 Hz), 7.30 (1H, m), 7.40 (1H, d, J=2 Hz), 7.71 (1H, s), 7.80 (1H, dd, J=2 and 9 Hz), 8.05 (1H, d, J=2 Hz).

EXAMPLE 34

N-(2-Methyl-1,2,3,4-tetrahydroisoquinolin-7-yl)-4-acetoxybenzamide $^1$H NMR (CDCl$_3$) δ: 2.34 (3H, s), 2.48 (3H, s), 2.73 (2H, t, J=6 Hz), 2.92 (2H, t, J=6 Hz), 3.62 (2H, s), 7.11 (1H, d, J=8 Hz), 7.21 (2H, m), 7.31 (1H, m), 7.43 (1H, s), 7.75 (1H, s), 7.88 (2H, m); m/z (CI: 325 (MH+; 100%).

EXAMPLE 35

N-(2-Methyl-1,2,3,4-tetrahydroisoquinolin-7-yl)-4-cyclopentyloxybenzamide $^1$H NMR (CDCl$_3$) δ: 1.56–1.68 (2H, bm), 1.74–1.97 (6H, bm), 2.61 (3H, s), 2.95 (4H, m), 3.79 (2H, s), 4.81 (1H, m), 6.38 (1H, s), 6.54 (1H, dd, J=2 and 8 Hz), 6.85 (2H, m), 6.93 (2H, d, J=8 Hz), 7.95 (2H, d, J=8 Hz); m/z (CI): 349 (MH+; 20%).

EXAMPLE 36

N-(2-Methyl-1,2,3,4-tetrahydroisoquinolin-7-yl)-4-cyclopropylmethoxybenzamide $^1$H NM (CDCl$_3$) δ: 0.36 (2H, m), 0.66 (2H, m), 1.28 (1H, m), 2.44 (3H, s), 2.81 (2H, t, J=6 Hz), 2.89 (2H, t, J=6 Hz), 3.51 (2H, s), 3.86 (2H, m), 6.34 (1H, d, J=2 Hz), 6.50 (1H, dd, J=2 and 8 Hz), 6.92 (2H, m), 7.06 (1H, d, J=8 Hz), 7.31 (1H, dd, J=2 and 8 Hz), 7.82 (1H, m), 8.00 (1H, m); m/z (CI): 337 (MH$^+$; 100%).

EXAMPLE 37

N-(2-Methyl-1,2,3,4-tetrahydroisoquinolin-7-yl)-3-cyano-4-methoxybenzamide $^1$H NMR (CDCl$_3$) δ: 2.47 (3H, s), 2.70 (2H, t, J=6 Hz), 2.91 (2H, t, J=6 Hz), 3.59 (2H, s), 4.02 (3H, s), 7.09 (2H, t, J=8 Hz), 7.29 (1H, dd, J=2 and 8 Hz), 7.39 (1H, d, J=2 Hz), 7.80 (1H, s), 8.10 (2H, m); m/z (CI): 322 (MH$^+$; 100)%).

EXAMPLE 38

N-(2-Methyl-1,2,3,4-tetrahydroisoquinolin-7-yl)-2-naphthamide $^1$H NMR (CDCl$_3$) δ: 2.50 (3H, s), 2.75 (2H, t, J=6 Hz), 2.94 (2H, t, J=6 Hz), 3.65 (2H, s), 7.13 (1H, d, J=8 Hz), 7.38 (1H, dd, J=2 and 8 Hz), 7.50 (1H, d, J=2 Hz), 7.56–7.22 (3H, bm), 7.88–8.07 (4H, bm), 8.38 (1H, s); m/z (CI): 317 (MH$^+$; 100%).

EXAMPLE 39

N-(2-Methyl-1,2,3,4-tetrahydroisoquinolin-7-yl)-3-bromo-4-methybenzamide $^1$H NMR (CDCl$_3$) δ: 2.47 (6H, bs), 2.71 (2H, t, J=6 Hz), 2.91 (2H, t, J=6 Hz), 3.60 (2H, s), 7.10 (1H, d, J=8 Hz), 7.23–7.39 (2H, bm), 7.42 (1H, s), 7.70 (2H, dd, J=2 and 8 Hz), 8.02 (1H, d, J=2 Hz); m/z (CI): 359, 361 (MH$^+$; 100%).

EXAMPLE 40

N-(2-Methyl-1,2,3,4-tetrahydroisoquinolin-7-yl)-naphthalene-1-carboxamide $^1$H NMR (CDCl$_3$) δ: 2.50 (3H, s), 2.75 (2H, t, J=6 Hz), 2.92 (2H, t, J=6 Hz), 3.66 (2H, s), 7.12 (1H, d, J=8 Hz), 7.35 (1H, d, J=8 Hz), 7.45–7.70 (5H, m), 7.75 (1H, d, J=8 Hz), 7.90 (1H, m), 7.96 (1H, d, J=7 Hz), 8.36 (1H, d, J=8 Hz). m/z (API$^+$): 317.2 (MH$^+$; 100%).

EXAMPLE 41

N-(2-Methyl-1,2,3,4-tetrahydroisoquinolin-7-yl)-3-chloro-4-methoxybenzamide $^1$H NMR (CDCl$_3$) δ: 2.47 (3H, s), 2.70 (2H, t, J=6 Hz), 2.91 (2H, t, J=6 Hz), 3.59 (2H, s), 3.97 (3H, s), 6.99 (1H, d, J=9 Hz), 7.09 (1H, d, J=8 Hz), 7.32 (1H, dd, J=2 and 8 Hz), 7.40 (1H, s), 7.79 (2H, m), 7.90 (1H, d, J=2 Hz).

EXAMPLE 42

N-(2-Methyl-1,2,3,4-tetrahydroisoquinolin-7-yl)-4-tert-butoxybenzamide $^1$H NMR (CDCl$_3$) δ: 1.41 (9H, s), 2.47 (3H, s), 2.71 (2H, t, J=6 Hz), 2.91 (2H, t, J=6 Hz), 3.61 (2H, s), 7.03–7.12 (3H, b m), 7.30 (1H, dd, J=2 and 8 Hz), 7.43 (1H, d, J=2 Hz), 7.68 (1H, s), 7.79 (2H, d, J=9 Hz); m/z (CI): 339 (MH$^+$; 100%).

EXAMPLE 43

N-(2-Methyl-1,2,3,4-tetrahydroisoquinolin-7-yl)-4-n-propoxybenzamide $^1$H NMR (CDCl$_3$) δ: 1.01 (3H, t, J=7 Hz), 1.83 (2H, m), 2.87 (3H, s), 3.19 (2H, m), 3.44 (2H, t, J=7 Hz), 3.61 (2H, s), 3.87 (2H, m), 4.40 (2H, s), 6.93 (2H, d), 7.09 (1H, d), 7.51 (1H, dd, J=8, 2 Hz), 7.61 (1H, d), 7.92 (2H, d), 8.39 (1H, s).

EXAMPLE 44

N-(2-Methyl-1,2,3,4-tetrahydroisoquinolin-7-yl) benzotriazole-5-carboxamide m/z (CI): 308 (MH$^+$; 65%).

EXAMPLE 45

N-(2-Methyl-1,2,3,4-tetrahydroisoquinolin-7-yl) benzothiazol-6-carboxamide $^1$H NMR (CDCl$_3$) δ: 2.48 (3H, s), 2.72 (2H, t, J=6 Hz), 2.93 (2H, t, J=6 Hz), 3.62 (2H, s), 7.13 (1H, d, J=8 Hz), 7.34 (1H, dd, J=2 and 8 Hz), 7.45 (1H, d, J=2 Hz), 7.88 (1H, s), 7.97 (1H, dd, J=2 and 8 Hz), 8.22 (1H, d, J=8 Hz), 8.56 (1H, d, J=2 Hz), 9.15 (1H, s); m/z (CI): 322 (MH$^-$: 100%).

EXAMPLE 46

N-(2-Methyl-1,2,3,4-tetrahydroisoquinolin-7-yl)-2,3-dihydrobenzofuran-5-carboxamide $^1$H NMR (CDCl$_3$) δ: 2.48 (3H, s), 2.73 (2H, t, J=6 Hz), 2.91 (2H, t, J=6 Hz), 3.27 (2H, t, J=9 Hz), 3.62 (2H, s), 4.66 (2H, t, J=9 Hz), 6.83 (1H, d, J=8 Hz), 7.08 (1H, d, J=8 Hz), 7.28 (1H, dd, J=2 and 8 Hz), 7.42 (1H, s), 7.64 (1H, d, J=8 Hz), 7.76 (2H, m). m/z (CI): 309 (MH$^+$; 100%).

EXAMPLE 47

N-(2-Methyl-1,2,3,4-tetrahydroisoquinolin-7-yl)-2-methylbenzimidazole-5-carboxamide $^1$H NMR (d$_4$MeOH) δ: 2.51 (3H, s), 2.61 (3H, s), 2.92 (2H, t, J=6 Hz), 2.96 (2H, t, J=6 Hz), 3.69 (2H, s), 7.14 (1H, d, J=9 Hz), 7.47 (3H, m), 7.56 (1H, d, J=8 Hz), 7.80 (1H, dd, J=2 and 8 Hz), 8.10 (1H, s); m/z (CI): 321 (MH$^+$; 100%).

EXAMPLE 48

N-(2-Methyl-1,2,3,4-tetrahydroisoquinolin-7-yl)-3-chloro-4-iso-propoxybenzamide $^1$H NMR (CDCl$_3$) δ: 1.42 (6H, d, J=6 Hz), 2.49 (3H, s), 2.74 (2H, t, J=6 Hz), 2.92 (2H, t, J=6 Hz), 3.63 (2H, s), 4.67 (1H, quintet, J=6 Hz), 6.98 (1H, d, J=9 Hz), 7.09 (1H, d, J=8 Hz), 7.28 (1H, dd, J=2 and 8 Hz), 7.40 (1H, d, J=2 Hz), 7.67–7.81 (2H, bm), 7.88 (1H, d, J=2 Hz); m/z (CI): 359 (MH$^+$; 100%).

EXAMPLE 49

N-(2-Methyl-1,2,3,4-tetrahydroisoquinolin-7-yl)-3-bromo-4-ethoxybenzamide $^1$H NMR (CDCl$_3$) δ: 1.51 (3H, t, J=7 Hz), 2.49 (3H, s), 2.74 (2H, t, J=6 Hz), 2.92 (2H, t, J=6 Hz), 3.62 (2H, s), 4.17 (2H, q, J=7 Hz), 6.93 (1H, d, J=9 Hz), 7.09 (1H, d, J=8 Hz), 7.28 (1H, dd, J=2 and 8 Hz), 7.39 (1H, d, J=2 Hz), 7.71 (1H, s), 7.80 (1H, dd, J=2 and 9 Hz), 8.05 (1H, d, J=2 Hz); m/z (CI): 389, 391 (MH$^+$; 100%).

EXAMPLE 50

N-(2-Methyl-1,2,3,4-tetrahydroisoquinolin-7-yl)-3-chloro-4-ethoxybenzamide $^1$H NMR (CDCl$_3$) δ: 1.51 (3H, t, J=7 Hz), 2.49 (3H, s), 2.74 (2H, t, J=6 Hz), 2.92 (2H, t, J=6 Hz), 3.62 (2H, s), 4.18

(2H, q, J=7 Hz), 6.96 (1H, d, J=9 Hz), 7.09 (1H, d, J=8 Hz), 7.31 (1H, dd, J=2 and 8 Hz), 7.39 (1H, d, J=2 Hz), 7.76 (2H, m), 7.89 (1H, d, J=2 Hz); m/z (CI): 345 (MH$^+$; 100%).

EXAMPLE 51

N-(2-Methyl-1,2,3,4-tetrahydroisoquinolin-7-yl)-4-methoxy-3-trifluoromethylbenzamide $^1$H NMR (CDCl$_3$) δ: 2.48 (3H, s), 2.72 (2H, t, J=6 Hz), 2.92 (2H, t, J=6 Hz), 3.60 (2H, s), 3.98 (3H, s), 7.09 (2H, m), 7.32 (1H, dd, J=2 and 8 Hz), 7.41 (1H, d, J=2 Hz), 7.83 (1H, s), 8.07 (2H, m); m/z (CI): 365 (MH$^+$; 100%).

EXAMPLE 52

N-(2-Methyl-1,2,3,4-tetrahydroisoquinolin-7-yl)-3,5-dichloro-4-methoxybenzamide $^1$H NMR (CDCl$_3$) δ: 2.46 (3H, s), 2.69 (2H, t, J=6 Hz), 2.90 (2H, t, J=6 Hz), 3.57 (2H, s), 3.96 (3H, s), 7.09 (1H, d, J=8 Hz), 7.30 (1H, dd, J=2 and 8 Hz), 7.34 (1H, d, J=2 Hz), 7.81 (2H, s), 7.89 (1H, s); m/z (CI): 365 (MH$^+$; 100%).

EXAMPLE 53

N-(2-Methyl)-1,2,3,4-tetrahydroisoquinolin-7-yl)-3,5-dichloro-4-ethoxybenzamide $^1$H NMR (CDCl$_3$) δ: 1.49 (3H, t, J=7 Hz), 2.46 (3H, s), 2.69 (2H, t, J=7 Hz), 2.90 (2H, t, J=6 Hz), 3.56 (2H, s), 4.17 (2H, q, J=7 Hz), 7.09 (1H, d, J=8 Hz), 7.29 (1H, dd, J=2 and 8 Hz), 7.32 (1H, s), 7.80 (2H, s), 7.86 (1H, s); m/z (CI): 379 (MH$^+$; 100%).

EXAMPLE 54

N-(2-Methyl)-1,2,3,4-tetrahydroisoquinolin-7-yl)-3,5-dichloro-4-iso-propoxybenzamide $^1$H NMR (CDCl$_3$) δ: 1.39 (6H, d, J=6 Hz), 2.47 (3H, s), 2.70 (2H, t, J=6 Hz), 2.91 (2H, t, J=6 Hz), 3.59 (2H, s), 4.72 (1H, quintet, J=6 Hz), 7.10 (1H, d, J=8 Hz), 7.30 (1H, dd, J=2 and 8 Hz), 7.36 (1H, s), 7.76 (d, J=2 Hz), 7.80 (2H, s). m/z (CI): 393 (MH$^+$; 100%).

EXAMPLE 55

N-(2-Methyl-1,2,3,4-tetrahydroisoquinolin-7-yl)-3-methylsulfonylbenzamide $^1$H NMR (CDCl$_3$) δ: 2.48 (3H, s), 2.71 (2H, t, J=6 Hz), 2.92 (2H, t, J=6 Hz), 3.12 (3H, s), 3.60 (2H, s), 7.12 (1H, d, J=8 Hz), 7.35 (1H, dd, J=2 and 8 Hz), 7.42 (1H, s), 7.73 (1H, t, J=8 Hz), 8.05 (1H, s), 8.11 (1H, d, J=8 Hz), 8.22 (1H, d, J=8 Hz), 8.40 (1H, s); m/z (CI): 345 (MH$^+$; 100%).

EXAMPLE 56

N-(2-methyl-1,2,3,4-tetrahydroisoquinolin-7-yl)-3-bromo-4-tert-butylbenzamide

A solution of the amine D5 (162 mg; 1.0 mmol) and 3-bromo-4-tert-butylbenzoic acid (257 mg; 1.0 mmol) in anhydrous N,N-dimethylformamide (7 ml), was treated with 1-hydroxybenzotriazole (135 mg; 1.0 mmol) and 1-(3-Dimethylaminopropyl)-3-ethylcarbodiimide (192 mg; 1.0 mmol) at 25° C. The mixture was shaken for 48 h before extracting the product into dichloromethane and washing with 10% aqueous NaHCO$_3$, water and finally brine. The organic layer was dried over MgSO$_4$ and evaporated in vacuo to afford 373 mg of the title compound in 93% yield.

$^1$H NMR (CDCl$_3$) δ: 1.54 (9H, s), 2.47 (3H, s), 2.71 (2H, t, J=6 Hz), 2.91 (2H, t, J=6 Hz), 3.60 (2H, s), 7.10 (1H, d, J=8 Hz), 7.31 (1H, dd, J=2 and 8 Hz), 7.41 (1H, d, J=2 Hz), 7.54 (1H, d, J=8 Hz), 7.72 (2H, m), 8.06 (1H, d, J=2 Hz).

EXAMPLE 57

N-(2-Methyl-1,2,3,4-tetrahydroisoquinolin-7-yl)-2-bromo-5-methoxybenzamide $^1$H NMR (CDCl$_3$) δ: 2.47 (3H, s), 2.70 (2H, t, J=6 Hz), 2.91 (2H, t, J=6 Hz), 3.61 (2H, s), 3.83 (3H, s), 6.88 (1H, dd), 7.11 (1H, d, J=8 Hz), 7.21 (1H, d), 7.31 (1H, dd, J=8, 2 Hz), 7.44 (1H, d,), 7.50 (1H, d), 7.71 (1H, s); m/z (API+): 375.0 (MH$^+$; 100%).

EXAMPLE 58

N-(2-Methyl-1,2,3,4-tetrahydroisoquinolin-7-yl)-4-fluoro-3-methoxybenzamide, hydrochloride $^1$H NMR (free base CDCl$_3$) δ: 2.53 (3H, s), 2.76 (2H, t, J=6 Hz), 2.97 (2H, t, J=6 Hz), 3.63 (2H, s), 4.01 (3H, s), 7.16 (1H, dd, J=6, 2 Hz), 7.21 (1H, d), 7.32–7.50 (3H, m), 7.64 (1H, dd, J=6, 2 Hz), 8.00 (1H, brs); m/z (API+): 315.1 (MH$^+$; 100%).

EXAMPLE 59

N-(2-Methyl-1,2,3,4-tetrahydroisoquinolin-7-yl)-1-methylpyrazole-4-carboxamide $^1$H NMR (250 MHz, CDCl$_3$) δ: 2.30 (3H, s), 2.53 (2H, m), 3.40 (2H, s), 3.78 (3H, s), 6.91 (1H, d, J=8 Hz), 7.11 (1H, m), 7.21 (1H, d), 7.20 (1H, brs), 7.46 (1H, br), 7.68 (1H, s), 7.76 (1H, s); m/z (API+): 271 (MH$^+$; 100%).

EXAMPLE 60

N-(2-Methyl-1,2,3,4-tetrahydroisoquinolin-7-yl)-4-trifluoromethylpyrazole-3-carboxamide $^1$H NMR (250 MHz, D$_6$ DMSO) δ: 2.41 (3H, s), 2.81–2.85 (4H, m), 7.13 (1H, d, J=8 Hz), 7.46 (2H, m), 8.64 (1H, s); m/z (API+): 325 (MH$^+$; 100%).

EXAMPLE 61

N-(2-Methyl-1,2,3,4-tetrahydroisoquinolin-7-yl)-2-methylthiazole-4-carboxamide $^1$H NMR (250 MHz, CDCl$_3$) δ: 2.47 (3H, s), 2.67–2.76 (5H, m), 2.89 (2H, m), 3.60 (2H, s), 7.10 (1H, d, J=8 Hz), 7.40 (1H, dd, J=8, 2 Hz), 7.49 (1H, brs), 8.02 (1H, br), 9.12 (1H, br); m/z (API+): 288 (MH$^+$; 100%).

EXAMPLE 62

N-2-Methyl-1,2,3,4-tetrahydroisoquinolin-7-yl)-5-methylisoxazole-3-carboxamide $^1$H NMR (250 MHz, CDCl$_3$) δ: 2.46 (3H, s), 2.51 (3H, s), 2.68 (2H, m), 2.90 (2H, m), 3.58 (2H, s), 6.51 (1H, s), 7.10 (1H, d, J=8 Hz), 7.33 (1H, dd, J8, 2 Hz), 7.41 (1H, brs), 8.47 (1H, brs); m/z (API+): 272 (MH$^+$; 100%).

EXAMPLE 63

N-(2-Methyl-1,2,3,4-tetrahydroisoquinolin-7-yl)-5-tert-butylisoxazole-3-carboxamide $^1$H NMR (250 MHz, CDCl$_3$) δ: 1.38 (9H, s), 2.46 (3H, s), 2.66–2.71 (2H, m), 2.89 (2H, m), 3.59 (2H, s), 6.48 (1H, s), 7.10 (1H, d, J=8 Hz), 7.30 (2H, brd, J=8 Hz), 7.41 (1H, brs), 8.43 (1H, brs); m/z (API+): 314 (MH+; 100%).

EXAMPLE 64

N-(2-Methyl-1,2,3,4-tetrahydroisoquinolin-7-yl)-3-methoxyisoxazole-5-carboxamide hydrochloride $^1$H NMR (250 MHz, DMSO-$d_6$) δ: inter alia 2.81 (3H, brs), 3.88 (3H, s), 7.00 (1H, s), 7.16 (2H, d, J=8 Hz), 7.52 (2H, m); m/z (API+): 288 (MH+; 100%).

EXAMPLE 65

N-(2-methyl-1,2,3,4-tetrahydroisoquinolin-7-yl) indole-2-carboxamide

D5 was converted into the title compound by reaction with indole-2-carboxylic acid, in a similar manner to the procedure of Description 7.

$^1$H NMR ($D_6$ DMSO) δ: 2.84 (3H, s), 3.07 (2H, t, J=6 Hz), 3.29 (2H, t, J=6 Hz), 3.97 (2H, s), 5.01 (1H, m), 7.53 (2H, m), 7.70 (2H, m), 8.08 (4H, m), 9.90 (1H, brs). m/z (API+): 306 (MH+; 100%).

EXAMPLE 66

N-(2-Methyl-1,2,3,4-tetrahydroisoquinolin-7-yl)-3-bromo-4-iso-propylbenzamide, hydrochloride $^1$H NMR (free base, CDCl$_3$) δ: 1.26 (6H, d, J=7 Hz), 2.48 (3H, s), 2.75 (2H, m), 2.90 (2H, m), 3.41 (1H, sep, J=7 Hz), 3.62 (2H, s), 7.09 (1H, d, J=8 Hz), 7.31 (2H, dd, J=8.2 Hz), 7.37 (2H, m), 7.76 (1H, dd, J=8.2 Hz), 7.90 (1H, brs), 8.02 (1H, d, J=2 Hz); m/z (API+): 387, 389 (MH+; 100%).

EXAMPLE 67

N-(2-Methyl-1,2,3,4-tetrahydroisoquinolin-7-yl)-3-cyano-4-iso-propylbenzamide, hydrochloride $^1$H NMR (free base, CDCl$_3$) δ: 1.25 (6H, d, J=7 Hz), 2.37 (3H, s), 2.60 (2H, m), 2.80 (2H, m), 3.45 (1H, sep, J=7 Hz), 3.62 (2H, s), 7.00 (1H, d, J=8 Hz), 7.25 (2H, m), 7.41 (1H, d), 7.97 (1H, dd, J=8.2 Hz), 8.03 (1H, d, J=2 Hz), 8.10 (1H, brs); m/z (API+): 334 (MH+; 100%).

EXAMPLE 68

N-(2-Methyl-1,2,3,4-tetrahydroisoquinolin-7-yl)-3-fluoro-4-methoxybenzamide $^1$H NMR (250 MHz CDCl$_3$) δ: 2.48 (3H, s), 2.73 (2H, t, J=6 Hz), 2.92 (2H, t, J=6 Hz), 3.61 (2H, s), 3.96 (3H, s), 7.05 (2H, m), 7.30 (1H, dd, J=6.2 Hz), 7.40 (1H, s), 7.63 (2H, d), 7.80 (1H, d); m/z (API+): 315.2 (MH+; 100%).

EXAMPLE 69

N-(2-Methyl-1,2,3,4-tetrahydroisoquinolin-7-yl)-3-cyano-4-n-propoxybenzamide $^1$H NMR (250 MHz CDCl$_3$) δ: 1.10 (3H, t, J=8 Hz), 1.92 (2H, m), 2.47 (3H, s), 2.70 (2H, t, J=6 Hz), 2.90 (2H, t, J=6 Hz), 3.58 (2H, s), 4.10 (2H, J=8 Hz), 7.02 (1H, d,), 7.09 (1H, d), 7.33 (1H, dd, J=6, 2 Hz), 7.38 (1H, s), 8.02 (1H, s), 8.08 (2H, m); m/z (API+): 350.2 (MH+; 100%).

EXAMPLE 70

N-2-Methyl-1,2,3,4-tetrahydroisoquinolin-7-yl)-3-cyano-4-ethoxybenzamide $^1$H NMR (250 MHz CDCl$_3$) δ: 1.53 (3H, t, J=8 Hz), 2.49 (3H, s), 2.74 (2H, t, J=6 Hz), 2.92 (2H, t, J=6 Hz), 3.62 (2H, s), 4.23 (2H, q, J=8 Hz), 7.04 (1H, d), 7.10 (1H, d), 7.32 (1H, dd, J=6.2 Hz), 7.40 (1H, d), 7.92 (1H, s), 8.09 (2H, m); m/z (API+): 336.2 (MH+; 100%).

EXAMPLE 71

N-(2-Methyl-1,2,3,4-tetrahydroisoquinolin-7-yl)-3-bromo-4-n-propoxybenzamide $^1$H NMR (250 MHz CDCl$_3$) δ: 1.10 (3H, t, J=8 Hz), 1.90 (2H, m), 2.46 (3H, s), 2.69 (2H, t, J=6 Hz), 2.90 (2H, t, J=6 Hz), 3.58 (2H, s), 4.05 (2H, t, J=8 Hz), 6.93 (1H, d), 7.09 (1H, d), 7.30 (1H, dd, J=6, 2 Hz), 7.39 (1H, d), 7.72 (1H, s), 7.80 (H, dd, J=6, 2 Hz), 8.05 (1H, d); m/z (API+): 403.1 (MH+; 90%).

EXAMPLE 72

N-(2-Methyl-1,2,3,4-tetrahydroisoquinolin-7-yl)-3-bromo-4-ethylbenzamide $^1$H NMR (250 MHz CDCl$_3$) δ: 1.26 (3H, t, J=8 Hz), 2.46 (3H, s), 2.69 (2H, t, J=6 Hz), 2.82 (2H, q, J=8 Hz), 2.90 (2H, t, J=6 Hz), 3.59 (2H, s), 7.10 (1H, d), 7.28 (1H, dd, J=6, 2 Hz), 7.34 (1H, d), 7.41 (1H, d), 7.74 (2H, dd), 8.03 (1H, s); m/z (API+): 373.1 (MH+; 100%).

EXAMPLE 73

N-(2-Methyl-1,2,3,4-tetrahydroisoquinolin-7-yl)-3-iodo-4-methoxybenzamide $^1$H NMR (250 MHz CDCl$_3$) δ: 2.50 (3H, s), 2.79 (2H, t, J=6 Hz), 2.93 (2H, t, J=6 Hz), 3.64 (2H, s), 3.94 (3H, s), 6.85 (1H, d), 7.21 (1H, d), 7.08 (1H, d), 7.34 (1H, dd, J=6, 2 Hz), 7.38 (1H, d), 7.89 (1H, dd), 8.12 (1H, s), 8.29 (1H, d); m/z (API+): 423.0 (MH+; 100%).

EXAMPLE 74

N-(2-Methyl-1,2,3,4-tetrahydroisoquinolin-7-yl)-4-iso-propoxy-3-trifluoromethylbenzamide $^1$H NMR (250 MHz CDCl$_3$) δ: 1.39 (6H, d, J=8 Hz), 2.48 (3H, s), 2.70 (2H, t, J=6 Hz), 2.87 (2H, t, J=6 Hz), 3.54 (2H, s), 4.72 (1H, m), 7.06 (2H, t), 7.30 (1H, dd, J=6, 2 Hz), 7.37 (1H, s), 8.03 (3H, m); m/z (API+): 393.2 (MH+; 100%).

EXAMPLE 75

N-(2-Methyl-1,2,3,4-tetrahydroisoquinolin-7-yl)-4-chloro-3-methoxybenzamide $^1$H NMR (250 MHz CDCl$_3$) δ: 2.47 (3H, s), 2.70 (2H, t, J=6 Hz), 2.88 (2H, t, J=6 Hz), 3.59 (2H, s), 3.98 (3H, s), 7.11 (1H, d), 7.21 (1H, d), 7.30 (2H, m), 7.40 (1H, d), 7.45 (1H, d), 7.75 (1H, s); m/z (API+): 331.1 (MH+; 100%).

EXAMPLE 76

N-(2-Methyl-1,2,3,4-tetrahydroisoquinolin-7-yl)-4-n-propoxy-3-trifluoromethylbenzamide $^1$H NMR (250 MHz CDCl$_3$) δ: 1.08 (3H, t, J=8 Hz), 1.86 (2H, m), 2.46 (3H, s), 2.70 (2H, t, J=6 Hz), 2.90 (2H, t, J=6 Hz), 3.58 (2H, s), 4.08 (2H, t, J=8 Hz), 7.07 (2H, m), 7.29 (1H, dd, J=6, 2 Hz), 7.41 (1H, d), 7.97 (1H, s), 8.03 (1H, d), 8.07 (1H, s); m/z (API+): 393.2 (MH+; 100%).

EXAMPLE 77

N-(2-Methyl-1,2,3,4-tetrahydroisoquinolin-7-yl)-3-chloro-4-tert-butylbenzamide, hydrochloride $^1$H NMR (250 MHz, DMSO-$d_6$) δ: inter alia 1.68 (9H, s), 7.36 (1H, d, J=8 Hz), 7.77 (3H, m), 8.00 (1H, dd, J=8, 2 Hz), 8.11 (1H, d, J=2 Hz); m/z (API+): 357 (MH+; 100%).

EXAMPLE 78

N-(2-Methyl-1,2,3,4-tetrahydroisoquinolin-7-yl)-4-methoxybenzamide hydrochloride D5 was converted into the title compound in 95% yield by reaction with 4-methoxybenzoyl chloride in a manner similar to that described in Example 3.

$^1$H NMR (D$_2$O) δ: 3.13 (3H, s), 3.25 (2H, brs), 3.68 (2H, brs), 3.96 (3H, s), 4.48 (2H, brs), 7.15 (2H, d, J=9 Hz), 7.35–7.50 (3H, m), 7.90 (2H, d, J=9 Hz).

EXAMPLE 79

N-(2-Methyl-1,2,3,4-tetrahydroisoquinolin-7-yl)-4-fluoro-3-methylbenzamide, hydrochloride $^1$H NMR (free base CDCl$_3$) δ: 2.34 (3H, s), 2.46 (3H, s) 2.69 (2H, t, J=6 Hz), 2.90 (2H, t, J=6 Hz), 3.58 (2H, s), 7.08 (2H, m), 7.30 (1H, dd), 7.40 (1H, d), 7.60–7.80 (2H, m), 7.74 (1H, s); m/z (API+): 299.2 (MH$^+$; 100%).

EXAMPLE 80

N-(2-Methyl-1,2,3,4-tetrahydroisoquinolin-7-yl)-3-chloro-4-iso-propylbenzamide $^1$H NMR (free base 250 MHz CDCl$_3$) δ: 1.40 (6H, d, J=7 Hz), 2.59 (3H, s), 2.82 (2H, m), 3.03 (2H, m), 3.58 (1H, sep, J=7 Hz), 3.71 (2H, s), 7.23 (1H, d, J=8 Hz), 7.42 (1H, dd, J=8, 2 Hz), 7.53 (2H, m), 7.82 (2H, m), 7.96 (1H, d, J=2 Hz); m/z (API+): 343, 345 (MH$^+$; 100, 50%).

EXAMPLE 81

N-(2-Methyl-1,2,3,4-tetrahydroisoquinolin-7-yl)-3-cyano-4-ethylbenzamide hydrochloride $^1$H NMR (free base 250 MHz, CDCl$_3$) δ: 1.31 (3H, t, J=8 Hz), 2.43 (3H, s), 2.66 (2H, m), 2.90 (4H, m), 3.55 (2H, s), 7.09 (1H, d, J=8 Hz), 7.28 (2H, dd, J=8, 2 Hz), 7.36 (1H, brs), 7.44 (1H, d, J=8 Hz), 7.86 (1H, brs), 8.00 (1H, dd, J=8.2 Hz), 8.09 (1H, d, J=2 Hz); m/z (API+): 320 (MH$^+$; 100%).

EXAMPLE 82

N-(2-Methyl-1,2,3,4-tetrahydroisoquinolin-7-yl)-4-iso-propyl-3-trifluoromethylbenzamide hydrochloride $^1$H NMR (free base 250 MHz, CDCl$_3$) δ: inter alia 1.38 (6H, d, J=6 Hz), 2.32 (3H, s), 2.57 (2H, m), 2.76 (2H, m), 3.25 (1H, m), 3.45 (2H, s), 6.95 (1H, d, J=8 Hz), 7.16 (1H, brd, J=8 Hz), 7.26 (1H, brs), 7.43 (1H, d, J=8 Hz), 7.72 (1H, brs), 7.84 (1H, d, J=8 Hz), 7.93 (1H, brs); m/z (API+): 377 (MH$^+$; 100%).

EXAMPLE 83

N-(2-Methyl-1,2,3,4-tetrahydroisoquinolin-7-yl)-4-ethyl-3-trifluoromethylbenzamide hydrochloride $^1$H NMR (free base 250 MHz, CDCl$_3$) δ: inter alia 1.25 (3H, t, J=8 Hz), 2.46 (3H, s), 2.68 (2H, m), 2.90 (2H, m), 3.58 (2H, brs), 7.10 (1H, d, J=8 Hz), 7.30 (1H, dd, J=8, 2 Hz), 7.47 (1H, d, J=8 Hz), 7.40 (1H, brs), 7.78 (1H, brs), 7.97 (1H, dd), 8.08 (1H, brs); m/z (API-): 361 (MH$^-$; 100%).

EXAMPLE 84

N-(2-Methyl-1,2,3,4-tetrahydroisoquinolin-7-yl)-3-cyano-4-iso-propoxybenzamide hydrochloride $^1$H NMR (250 MHz CDCl$_3$) δ: 1.45 (6H, d, J=8 Hz), 2.47 (3H, s), 2.70 (2H, t, J=6 Hz), 2.91 (2H, t, J=6 Hz), 3.59 (2H, s), 4.75 (1H, m), 7.04 (1H, d), 7.10 (1H, d), 7.29 (1H, dd, J=6, 2 Hz), 7.37 (1H, d), 7.71 (1H, s), 8.05 (2H, m); m/z (API+): 350.2 (MH$^+$; 100%).

EXAMPLE 85

N-(1,2,3,4-Tetrahydroisoquinolin-7-yl)-4-methoxy-3-trifluoromethylbenzamide $^1$H NMR (250 MHz CDCl$_3$) δ: 2.65 (2H, t, J=6 Hz), 3.00 (2H, t, J=6 Hz), 3.85 (3H, s), 3.89 (2H, s), 6.95 (2H, d), 7.17 (1H, dd, J=6, 2 Hz), 7.25 (1H, s), 7.57 (1H, s), 7.93 (2H, m); m/z (API+): 351.1 (MH$^+$; 100%)

EXAMPLE 86

N-(2-Methyl-1,2,3,4-tetrahydroisoquinolin-7-yl)-4-methyl-3-methylsulfonylbenzamide $^1$H NMR (CDCl$_3$) δ: 2.48 (3H, s), 2.71 (2H, t, J=7 Hz), 2.80 (3H, s), 2.92 (2H, t, J=7 Hz), 3.15 (3H, s), 3.61 (2H, s), 7.13 (2H, d), 7.35 (1H, dd), 7.43 (1H, s), 7.52 (1H, d), 7.93 (1H, s), 8.14 (1H, dd), 8.45 (1H, d); m/z (API$^+$): 359.2 (MH$^+$; 100%).

EXAMPLE 87

N-(2-Methyl-1,2,3,4-tetrahydroisoquinolin-7-yl)-4-ethyl-3-methylsulfonylbenzamide $^1$H NMR (CDCl$_3$) δ: 1.49 (3H, t, J=8 Hz), 2.59 (3H, s), 2.81 (2H, t, J=7 Hz), 3.03 (2H, t, J=7 Hz), 3.27 (5H, m), 3.71 (2H, s), 7.23 (2H, d), 7.46 (1H, dd), 7.54 (1H, d), 7.69 (1H, d), 8.04 (1H, s), 8.29 (1H, dd), 8.55 (1H, d); m/z (API$^+$): 373.2 (MH$^+$; 100%).

EXAMPLE 88

N-(2-Methyl-1,2,3,4-tetrahydroisoquinolin-7-yl)-3-methylsulfonyl-4-iso-propylbenzamide $^1$H NMR (CDCl$_3$) δ: 1.27 (6H, d, J=8 Hz), 2.37 (3H, s), 2.60 (2H, t, J=7 Hz), 2.81 (2H, t, J=7 Hz), 3.06 (3H, s), 3.46 (2H, s), 3.85 (1H, m), 7.00 (2H, d), 7.26 (1H, dd), 7.31 (1H, d), 7.57 (1H, d), 8.10 (1H, dd), 8.21 (1H, s), 8.37 (1H, d); m/z (API$^+$): 387.2 (MH$^+$; 100%).

EXAMPLE 89

N-(2-Methyl-1,2,3,4-tetrahydroisoquinolin-7-yl)-3-methylsulfonyl-4-methoxybenzamide $^1$H NMR (CDCl$_3$) δ: 2.31 (3H, s), 2.54 (2H, t, J=7 Hz), 2.75 (2H, t, J=7 Hz), 3.09 (3H, s), 3.42 (2H, s), 3.87 (3H, s), 6.95 (2H, m), 7.12 (1H, s), 7.21 (1H, d), 8.08 (2H, m), 8.23 (1H, d); m/z (API$^+$): 375.2 (MH$^+$; 75%).

EXAMPLE 90

N-(2-Methyl-1,2,3,4-tetrahydroisoquinolin-7-yl)-3-trifluoroacetylbenzamide, hydrochloride $^1$H NMR (free base CDCl$_3$) δ: 2.47 (3H, s), 2.46 (3H, s) 2.77 (2H, t, J=6 Hz), 2.94 (2H, t, J=6 Hz), 3.63 (2H, s), 7.13 (1H, d, J=6 Hz), 7.45 (1H, d, J=6 Hz), 7.54 (1H, t, J=6 Hz), 7.81 (1H, d, J=6 Hz), 7.97 (1H, d, J=6 Hz); 8.20 (1H, s); m/z (API+): 363.2 (MH$^+$; 60%).

EXAMPLE 91

N-(2-Methyl-1,2,3,4-tetrahydroisoquinolin-7-yl)-4-methoxy-3-pentafluoroethylbenzamide hydrochloride $^1$H NMR (free base 250 MHz, CDCl$_3$) δ: 2.46 (3H, s), 2.70 (2H, m), 2.90 (2H, m), 3.59 (2H, s), 3.94 (3H, s), 7.10

(2H, m), 7.30 (1H, dd, J=8, 2 Hz), 7.39 (1H, brs), 7.73 (1H, brs), 8.01 (1H, d, J=2 Hz), 8.06 (1H, dd, J=9, 2 Hz); m/z (API+): 415 (MH$^+$; 100%).

EXAMPLE 92

N-(2-n-Propyl-1,2,3,4-tetrahydroisoquinolin-7-yl)-3-bromo-4-ethoxybenzamide $^1$H NMR (CDCl$_3$) δ: 0.95 (3H, t, J=7 Hz), 1.51 (3H, t, J=7 Hz), 1.62 (2H, m), 2.47 (2H, t, J=8 Hz), 2.72 (2H, t, J=6 Hz), 2.88 (2H, t, J=6 Hz), 3.61 (2H, s), 4.17 (2H, q, J=7 Hz), 6.92 (1H, d, J=9 Hz), 7.07 (1H, d, J=8 Hz), 7.26 (1H, dd, J=8, 2 Hz), 7.39 (1H, d, J=2 Hz), 7.72 (1H, brs), 7.79 (1H, dd, J=9, 2 Hz), 8.04 (1H, d, J=2 Hz). m/z (API$^+$): 417, 419 (MH$^+$; 95%).

EXAMPLE 93

N-(2-n-Propyl-1,2,3,4-tetrahydroisoquinolin-7-yl)-4-methoxy-3-trifluoromethylbenzamide $^1$H NMR (CDCl$_3$) δ: 0.96 (3H, t, J=7 Hz), 1.61 (2H, m), 2.47 (2H, t, J=Hz), 2.73 (2H, J=6 Hz), 2.88 (2H, t, J=6 Hz), 3.62 (2H, s), 3.98 (3H, s), 7.08 (2H, m), 7.30 (1H, m), 7.41 (1H, d, J=2 Hz), 7.76 (1H, brs), 8.05 (2H, m); m/z (API$^+$): 393 (MH$^+$; 100%).

EXAMPLE 94

N-(2-n-Propyl-1,2,3,4-tetrahydroisoquinolin-7-yl)-3-chloro-4-iso-propoxybenzamide $^1$H NMR (CDCl$_3$) δ: 0.95 (3H, t, J=7 Hz), 1.42 (6H, d, J=6 Hz), 1.62 (2H, m), 2.48 (2H, t, J=8 Hz), 2.73 (2H, t, J=6 Hz), 2.88 (2H, t, J=6 Hz), 3.63 (2H, s), 4.66 (1H, sept, J=6 Hz), 6.98 (1H, d, J=9 Hz), 7.08 (1H, d, J=8 Hz), 7.26 (1H, m), 7.41 (1H, d, J=2 Hz), 7.65 (1H, brs), 7.73 (1H, dd, J=9, 2 Hz), 7.87 (1H, d, J=2 Hz). m/z (API$^+$): 387 (MH$^+$; 90%).

EXAMPLE 95

N-(2-Methyl-1,2,3,4-tetrahydroisoquinolin-7-yl)-3-cyano-4-iso-butylbenzamide hydrochloride $^1$H NMR (250 MHz, DMSO-d$_6$) δ: inter alia 0.95 (6H, d, J=7 Hz), 1.99 (1H, sep, J=7 Hz), 2.77 (2H, brs), 7.26 (1H, d, J=8 Hz), 7.65 (3H, m), 8.21 (1H, dd, J=8, 2 Hz), 8.41 (1H, d, J=8 Hz); m/z (API+): 348 (MH$^+$; 100%).

EXAMPLE 96

N-(2-Methyl-1,2,3,4-tetrahydroisoquinolin-7-yl)-4-iso-butyl-3-trifluoromethylbenzamide hydrochloride $^1$H NMR (250 MHz, DMSO-d$_6$) δ: inter alia 1.01 (6H, d, J=6.5 Hz), 2.09 (1H, sep, J=6.5 Hz), 7.35 (1H, d, J=8 Hz), 7.75 (3H, m), 8.32 (1H, d, J=8 Hz); m/z (API+): 391 (MH$^+$; 100%).

EXAMPLE 97

N-(2-Ethyl-1,2,3,4-tetrahydroisoquinolin-7-yl)-3-bromo-4-ethoxybenzamide $^1$H NMR (CDCl$_3$) δ: 1.20 (3H, t, J=7 Hz), 1.51 (3H, t, J=7 Hz), 2.61 (2H, q, J=7 Hz), 2.76 (2H, m), 2.90 (2H, m), 3.64 (2H, s), 4.16 (2H, q, J=7 Hz), 6.91 (1H, d, J=8 Hz), 7.07 (1H, d, J=8 Hz), 7.26 (1H, m), 7.40 (1H, d, J=2 Hz), 7.79 (2H, m), 8.05 (1H, d, J=2 Hz); m/z (API$^+$): 403, 405 MH$^+$; 65%).

EXAMPLE 98

N-(2-Ethyl-1,2,3,4-tetrahydro-isoquinolin-7-yl)-4-methoxy-3-trifluoromethylbenzamide $^1$H NMR (CDCl$_3$) δ: 1.21 (3H, t, J=7 Hz), 2.65 (2H, q, J=7 Hz), 2.80 (2H, d, J=6 Hz), 2.92 (2H, t, J=6 Hz), 3.67 (2H, s), 3.97 (3H, s), 7.07 (2H, m), 7.30 (1H, m), 7.41 (1H, d, J=2 Hz), 7.89 (1H, brs), 8.06 (2H, m); m/z (API$^+$): 379 MH$^+$; 100%).

EXAMPLE 99

N-(2-iso-Propyl-1,2,3,4-tetrahydroisoquinolin-7-yl)-3-bromo-4-ethoxybenzamide $^1$H NMR (CDCl$_3$) δ: 1.13 (6H, d, J=7 Hz), 1.51 (3H, t, J=7 Hz), 2.84 (5H, m), 3.71 (2H, s), 4.16 (2H, q, J=7 Hz), 6.91 (1H, d, J=9 Hz), 7.06 (1H, d, J=8 Hz), 7.25 (1H, m), 7.42 (1H, d, J=2 Hz), 7.78 (2H, m), 8.04 (1H, d, J=2 Hz). m/z (API$^+$): 419 (MH$^+$; 90%).

EXAMPLE 100

N-(2-iso-Propyl-1,2,3,4-tetrahydroisoquinolin-7-yl)-4-methoxy-3-trifluoromethylbenzamide $^1$H NMR (CDCl$_3$) δ: 1.13 (6H, d, J=7 Hz), 2.84 (5H, m), 3.72 (2H, s), 3.97 (3H, s), 7.07 (2H, m), 7.26 (1H, m), 7.43 (1H, d, J=2 Hz), 7.83 (1H, brs), 8.04 (2H, m) m/z (API$^+$): 393 (MH$^+$; 100%).

EXAMPLE 101

N-(2-Methyl-1,2,3,4-tetrahydroisoquinolin-7-yl)-4-ethoxy-3-methylsulfonylbenzamide $^1$H NMR (CDCl$_3$) δ: 1.52 (3H, t, J=8 Hz), 2.46 (3H, s), 2.69 (2H, t, J=7 Hz), 2.90 (2H, t, J=7 Hz), 3.26 (3H, s), 3.57 (2H, s), 4.27 (2H, q, J=7 Hz), 7.09 (2H, dd), 7.36 (1H, dd), 7.42 (1H, s), 7.83 (1H, brs), 8.12 (1H, s), 8.20 (1H, dd), 8.37 (1H, d); m/z (API$^+$): 389.2 (MH$^+$; 100%).

EXAMPLE 102

N-(2-Methyl-1,2,3,4-tetrahydroisoquinolin-7-yl)-4-oxochroman-6-carboxamide hydrochloride $^1$H NMR (D$_6$ DMSO) δ: 2.63 (3H, narrow d), 3.02 (2H, t, J=7 Hz), 3.14 (2H, brm), 3.60 (2H, brm), 4.54 (2 h, brs), 4.77 (2H, d, J=7 Hz), 7.25 (1H, m), 7.31 (1H, d, J=8 Hz), 7.44 (2H, d, J=6 Hz), 8.20 (1H, dd, J=8, 2 Hz), 8.59 (1H, d, J=2 Hz), 10.31 (1H, s), 10.95 (1H, brs); m/z (API$^+$): 337.4 (MH$^+$; 100%).

EXAMPLE 103

N-(2-Formyl-1,2,3,4-tetrahydroisoquinolin-7-yl)-4-methoxy-3-trifluoromethylbenzamide 7-Amino-2-formyl-1,2,3,4-tetrahydroisoquinoline (0.176 g) was converted into the title compound by reaction with 4-methoxy-3-trifluoromethylbenzoyl chloride, following the procedure of Example 3. The product was isolated as a white solid (0.035 g).

$^1$H NMR (d$_6$-DMSO) δ: 2.80 (2H, m), 3.65 (2H, broad t), 4.00 (3H, s), 4.59 (2H, d), 7.17 (1H, d, J=8 Hz), 7.45 (1H, d, J=8 Hz), 7.60 (2H, m), 8.26 (3H, m), 10.30 (1H, s). m/z (API+): 379 (MH$^+$).

EXAMPLE 104

N-(2-Hydroxyethyl-1,2,3,4-tetrahydroisoquinolin-7-yl)-3-bromo-4-ethoxybenzamide

The compound D16 (115 mg; 0.22 mmol) was dissolved in THF with stirring and tetrabutylammonium fluoride (1 M in THF; 0.216 mmol) added. The reaction was stirred overnight and the mixture purified by column chromatography through SiO, eluting with 10% methanol:dichloromethane. Trituration with petroleum ether, gave the title compound (48 mg; 49%).

$^1$H NMR (250 MHz, CDCl$_3$) δ: 1.51 (3H, t, J=7 Hz), 2.77 (2H, t, J=5 Hz), 2.90 (4H, m, overlapping signal), 3.74 (4H, m, overlapping signal), 4.17 (2H, q, J=7 Hz), 6.93 (1H, d, J=10 Hz), 7.10 (1H, d, J=8 Hz), 7.36 (1H, dd, J=8.2 Hz), 7.48 (1H, d, J=2 Hz), 7.87 (1H, dd, J=9, 2 Hz), 7.97 (1H, s), 8.08 (1H, d, J=2 Hz).

EXAMPLE 105

N-(2-Hydroxyethyl-1,2,3,4-tetrahydroisoquinol-7-yl)-3-bromo-4-ethylbenzamide

The title compound was prepared in 40% overall yield from D15 in a manner similar to that of Descriptions 16 and Example 106.

$^1$H NMR (250 MHz, CDCl$_3$) δ: 2.77 (10H, m, overlapping signals), 3.68 (5H, m, overlapping signals), 7.08 (1H, d, J=8 Hz), 7.30 (2H, m, overlapping signals), 7.48 (1H, d, J=2 Hz), 7.75 (H, dd, J=8, 2 Hz), 8.02 (1H, d, J=2 Hz), 8.17 (1H, s).

EXAMPLE 106

N-(2-Methyl-1,2,3,4-tetrahydroisoquinolin-7-yl)-4-phenylmethoxy-3-trifluoromethylbenzamide $^1$H NMR (CDCl$_3$) δ: 2.50 (3H, s), 2.75 (2H, t, J=6 Hz), 2.94 (2H, t, J=6 Hz), 3.64 (2H, s), 7.10 (2H, d, J=8 Hz), 7.30–7.60 (7H, m, overlapping), 7.70 (1H, brs), 8.04 (1H, dd, J=8, 2 Hz), 8.10 (1H, d, J=2 Hz); m/z (CI): 441.2 (MH$^+$; 100%).

EXAMPLE 107

N-(2-Methyl-1,2,3,4-tetrahydroisoquinolin-7-yl)-4-hydroxy-3-trifluoromethylbenzamide m/z (CI): 351.1 (MH$^+$; 100%).

EXAMPLE 108

N-(2-Methoxyethyl-1,2,3,4-tetrahydroisoquinolin-7-yl)-3-bromo-4-iso-propoxybenzamide $^1$H NMR (250 MHz, CDCl$_3$) δ: 1.41 (6H, d, J=6 Hz), 2.75 (4H, t, overlapping, J=6 Hz), 2.83 (2H, d, J=5 Hz), 3.39 (3H, s), 3.61 (4H, t, overlapping, J=6 Hz), 4.64 (1H, m), 6.91 (1H, d, J=9 Hz), 7.01 (1, d, J=8 Hz), 7.20 (1H, dd, J=8, 2 Hz), 7.29 (1H, d, J=2 Hz), 7.80 (1H, dd, J=9, 2 Hz), 8.07 (1H, d, J=2 Hz), 8.10 (1H, s); m/z (API+): 447, 449 (MH+, 90%).

EXAMPLE 109

N-(2-Methoxyethyl-1,2,3,4-tetrahydroisoquinolin-7-yl)-3-chloro-4-iso-propoxybenzamide $^1$H NMR (250 MHz, CDCl$_3$) δ: 1.41 (6H, d, J=6 Hz), 2.75 (4H, t, overlapping, J=6 Hz), 2.83 (2H, d, J=5 Hz), 3.39 (3H, s), 3.61 (4H, t, overlapping, J=5 Hz), 4.64 (1H, m), 6.94 (1H, d, J=9 Hz), 7.01 (1H, d, J=8 Hz), 7.20 (1H, dd, J=8, 2 Hz), 7.30 (1H, s), 7.75 (1H, dd, J=9, 2 Hz), 7.90 (1H, d, J=2 Hz); m/z (API+): 403, 405 (MH+).

EXAMPLE 110

N-(2-Methoxyethyl-1,2,3,4-tetrahydroisoquinolin-7-yl)-4-methoxy-3-trifluoromethylbenzamide $^1$H NMR (250 MHz, CDCl$_3$) δ: 2.75 (4H, m), 2.85 (2H, d, J=5 Hz), 3.39 (3H, s), 3.61 (4H, t, overlapping), 3.96 (3H, s), 7.04 (2H, m), 7.25 (1H, d, J=10 Hz), 7.35 (1H, s), 8.07 (3H, m); m/z (API+): 409 (MH+, 100%).

EXAMPLE 111

(a) N-(2-t-Butyloxycarbonyl-5-iodo-1,2,3,4-tetrahydroisoquinolin-7-yl)-4-azidobenzamide The title compound was prepared in 81% yield from the acid Preparation 28 and amine D6.

(b) N-(5-Iodo-1,2,3,4-tetrahydroisoquinolin-7-yl)-4-azidobenzamide, trifluoroacetate The title compound was prepared in 91% yield from using a method similar to that of

EXAMPLE 1 m/z (CI): 420 (MH$^+$; 100%).

EXAMPLE 112

N-(2-Methyl-5-trifluoroacetylamino-1,2,3,4-tetrahydroisoquinolin-7-yl)-3-bromo-4-methoxybenzamide The title compound (0.66 g) was prepared from D25 (0.50 g) and 3-bromo-4-methoxybenzoic acid (0.63 g) using a procedure similar to that of Description 7.

m/z (CI): 486, 488 (MH$^+$; 90%).

EXAMPLE 113

N-(2-Methyl-5-chloro-1,2,3,4-tetrahydroisoquinolin-7-yl)-3-bromo-4-ethoxybenzamide m/z (CI): 425 (MH$^+$; expected isotope pattern).

EXAMPLE 114

N-(2-Methyl-5-chloro-1,2,3,4-tetrahydroisoquinolin-7-yl)-3-bromo-4-ethylbenzamide $^1$H NMR (CDCl$_3$) δ: 1.25 (3H, t, J=7 Hz), 2.48 (3H, s), 2.70–3.00 (6H, m, overlapping signals), 3.59 (2H, s), 7.29 (1H, d, J=2 Hz), 7.33 (1H, d, J=7 Hz), 7.51 (1H, d, J=2 Hz), 7.71 (1H, dd, J=7, 2 Hz), 7.83 (1H, brs), 8.01 (1H, d, J=2 Hz); m/z (CI): 409 (MH$^+$; expected isotope pattern).

Pharmacological Data

1. Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3]-Compound A, parallel assays are carried out as above in which [3H]-Compound A and tissue are incubated together in the presence of unlabelled Compound A (usually 3 $\mu$M). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active in this test. For example, compounds of Examples 1, 4, 5, 6, 7, 10 and 13 gave pKi values greater than 7.

2. MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

Method for Mouse Model

Mice (naive male, Charles River, U.K. CD1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

Studies are carried out using a Hugo Sachs Electronik Constant Current Shock Generator with totally variable control of shock level from 0 to 300 mA and steps of 2 mA are usually used.

Results

Compounds of this invention dosed at 10 mg/kg by the oral route as a suspension in methyl cellulose and tested one hour post dosing showed an increase in seizure threshold. For example, the compounds of Examples 4, 5, 6 and 7 show increases of 24%, 36%, 90% and 23% respectively.

Method for Rat Model

The threshold for maximal (tonic hindlimb extension) electroshock seizures in male rats (Sprague Dawley, 80–150 g, 6 weeks old) was determined by a Hugo Sachs Electronik stimulator which delivered a constant current (0.3 sec duration, from 1–300 mA in steps of 5–20 mA). The procedure is similar to that outlined above for mouse and full details are as published by Upton et al,.[4]

The percentage increase or decrease in $CC_{50}$ for each group compared to the control is calculated.

Drugs are suspended in 1% methyl cellulose.

Results

At a dosage of 2 mg/kg p.o. at 2 h, the compounds of Examples 48, 49, 51 and 67 show increases of 389%, 325%, 545% and 303% increases respectively.

References

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F. (1949). J. Pharmacol. exp. Ther., 96, 99–113
4. N. Upton, T. P. Blackburn, C. A. Campbell, D. Cooper, M. L. Evans, H. J. Herdon, P. D. King, A. M. Ray, T. O. Stean, W. N. Chan, J. M. Evans and M. Thompson. (1997). B. J. Pharmacol., 121, 1679–1686.

What is claimed is:

1. A method of treatment for the prophylaxis of disorders treatable or preventable with anti-convulsive agents, migraine, neuralgia, trigeminal neuralgia, neuropathic pain, dental pain, and cancer pain comprising administering to the sufferer in need thereof a prophylactic amount of a compound of formula (I) or a pharmaceutically acceptable salt thereof:

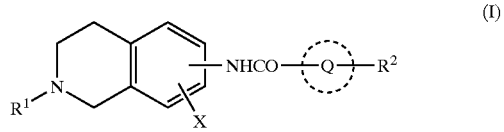

wherein:

Q is a monocyclic or bicyclic aryl or heteroaryl ring;

$R^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO$_2$—;

$R^2$ is hydrogen, hydroxy or up to three substituents selected from halogen, $NO_2$, CN, $N_3$, $CF_3O$—, $CF_3S$—, $CF_3CO$—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, acetoxy, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl)NHSO$_2$—, $(C_{1-4}$alkyl$)_2$NCO—, $(C_{1-4}$alkyl)NHCO— or CONH$_2$; or —NR$^3$R$^4$ where R$^3$ is hydrogen or $C_{1-4}$alkyl, and R$^4$ is hydrogen, $C_{1-4}$alkyl, formyl, —CO$_2$C$_{1-4}$alkyl or —COC$_{1-4}$alkyl; or two R$^2$ groups together form a carbocyclic ring that is saturated or unsaturated and unsubstituted or substituted by —OH or =O; and X is hydrogen, halogen, $C_{1-6}$alkoxy, $C_{1-6}$alkyl, amino or trifluoroacetylamino;

provided:

when X is hydrogen, R$^2$ is not 2-alkoxy; and when X is halogen the compound of formula (I) is not N-(7-iodo-2-methyl-1,2,3,4-tetrahydroisoquinolin-5-yl)-5-benzoyl-2-methoxybenzamide, N-(7-iodo-1,2,3,4-tetrahydroisoquinolin-5-yl)-5-benzoyl-2-methoxybenzamide, N-(5-iodo-1,2,3,4-tetrahydroisoquinolin-7-yl)-5-benzoyl-2-methoxybenzamide, N-(5-iodo-1,2,3,4-tetrahydroisoquinolin-7-yl)-2-methoxy-4-trifluoromethyldiazirinylbenzamide, N-(5-iodo-1,2,3,4-tetrahydroisoquinolin-7-yl)-2-methoxy-5-trifluoromethyldiazirinylbenzamide, N-(7-iodo-1,2,3,4-tetrahydroisoquinolin-5-y)-2-methoxy-5-trifluoromethyldiazirinylbenzamide or N-(8-fluoro-2-methyl-1,2,3,4-tetrahydroisoquinolin-5-yl)-4-t-butyl-2-methoxybenzamide.

2. A the method according to claim 1 wherein the compound of formula (I) is chosen from the compounds of formula (IA) or (IB):

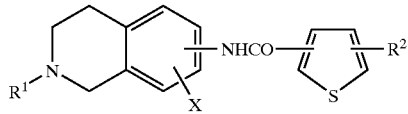
(IA)

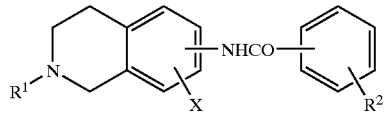
(IB)

wherein R$^1$, R$^2$ and X are as defined in claim 1.

3. A compound of formula (IA):

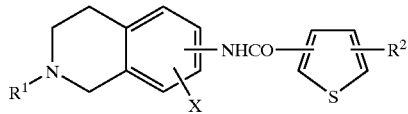
(IA)

wherein:

R$^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, CF$_3$CO— or $C_{1-6}$alkylSO$_2$—;

R$^2$ is hydrogen, hydroxy or up to three substituents selected from halogen, NO$_2$, CN, N$_3$, CF$_3$O—, CF$_3$S—, CF$_3$CO—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, acetoxy, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl)NHSO$_2$—, $(C_{1-4}$alkyl$)_2$NCO—, $(C_{1-4}$alkyl)NHCO— or CONH$_2$; or —NR$^3$R$^4$ where R$^3$ is hydrogen or $C_{1-4}$alkyl, and R$^4$ is hydrogen, $C_{1-4}$alkyl, formyl, —CO$_2$C$_{1-4}$alkyl or —COC$_{1-4}$alkyl; or two R$^2$ groups together form a carbocyclic ring that is saturated or unsaturated and unsubstituted or substituted by —OH or =O; and X is hydrogen, halogen, $C_{1-6}$alkoxy, $C_{1-6}$alkyl, amino or trifluoroacetylamino;

provided:

when X is hydrogen, R$^2$ is not 2-alkoxy;

or a pharmaceutically acceptable salt thereof.

4. A pharmaceutical composition which comprises a compound as defined in claim 3, or a pharmaceutically acceptable salt or solvate thereof, and a pharmaceutically acceptable carrier.

5. A compound chosen from the group consisting of:

N-(1,2,3,4-tetrahydroisoquinolin-7-yl)-5-chlorothiophene-2-carboxamide,

N-(2-methyl-1,2,3,4-tetrahydroisoquinolin-7-yl)-5-chlorothiophene-2-carboxamide, N-(2-methyl-1,2,3,4-tetrahydroisoquinolin-7-yl)benzamide, N-(2-methyl-1,2,3,4-tetrahydroisoquinolin-7-yl)-3-chlorobenzamide, N-(2-methyl-1,2,3,4-tetrahydroisoquinolin-7-yl)-4-t-butylbenzamide, N-(2-methyl-1,2,3,4-tetrahydroisoquinolin-7-yl)-4-iso-propoxybenzamide, N-(2-methyl-1,2,3,4-tetrahydroisoquinolin-7-yl)-4-phenoxybenzamide, N-(2-methyl-1,2,3,4-tetrahydroisoquinolin-7-yl)-4-nitrobenzamide, N-(2-methyl-1,2,3,4-tetrahydroisoquinolin-7-yl)-4-phenylbenzamide, N-(2-methyl-1,2,3,4-tetrahydroisoquinolin-7-yl)-3-methylbenzamide, N-(2-methyl-1,2,3,4-tetrahydroisoquinolin-7-yl)-3-fluorobenzamide, N-(2-methyl-1,2,3,4-tetrahydroisoquinolin-7-yl)-3-cyanobenzamide, N-(2-methyl-1,2,3,4-tetrahydroisoquinolin-7-yl)-3,4-dichlorobenzamide, N-(2-methyl-1,2,3,4-tetrahydroisoquinolin-7-yl)-4-iodobenzamide, N-(2-methyl-1,2,3,4-tetrahydroisoquinolin-7-yl)-4-bromobenzamide, N-(2-methyl-1,2,3,4-tetrahydroisoquinolin-7-yl)-4-methylbenzamide, N-(2-methyl-1,2,3,4-tetrahydroisoquinolin-7-yl)-3-nitrobenzamide, N-(2-methyl-1,2,3,4-tetrahydroisoquinolin-7-yl)-4-ethoxybenzamide, N-(2-methyl-1,2,3,4-tetrahydroisoquinolin-7-yl)-4-n-butylbenzamide, N-(2-methyl-1,2,3,4-tetrahydroisoquinolin-7-yl)-2-acetoxybenzamide, N-(2-methyl-1,2,3,4-tetrahydroisoquinolin-7-yl)-3-trifluoromethylbenzamide, N-(2-methyl-1,2,3,4-tetrahydroisoquinolin-7-yl)-2,4-difluorobenzamide, N-(2-methyl-1,2,3,4-tetrahydroisoquinolin-7-yl)-3,4-dimethoxybenzamide,
N-(2-methyl-1,2,3,4-tetrahydroisoquinolin-7-yl)-2-fluoro-4-trifluoromethylbenzamide,
N-(2-methyl-1,2,3,4-tetrahydroisoquinolin-7-yl)-4-chloro-3-nitrobenzamide,
N-(2-methyl-1,2,3,4-tetrahydroisoquinolin-7-yl)-3,5-di-trifluoromethylbenzamide,
N-(2-methyl-1,2,3,4-tetrahydroisoquinolin-7-yl)-2,4-dichloro-5-fluorobenzamide,
N-(2-methyl-1,2,3,4-tetrahydroisoquinolin-7-yl)-3-fluoro-5-trifluoromethylbenzamide,
N-(2-methyl-1,2,3,4-tetrahydroisoquinolin-7-yl)-3-bromo-4-methoxybenzamide,
N-(2-methyl-1,2,3,4-tetrahydroisoquinolin-7-yl)-4-trifluoromethoxybenzamide,
N-(2-methyl-1,2,3,4-tetrahydroisoquinolin-7-yl)-3-pivaloylbenzamide,
N-(2-Methyl-1,2,3,4-tetrahydroisoquinolin-7-yl)-3-bromo-4-iso-propoxybenzamide,
N-(2-Methyl-1,2,3,4-tetrahydroisoquinolin-7-yl)-4-acetoxybenzamide,
N-(2-Methyl-1,2,3,4-tetrahydroisoquinolin-7-yl)-4-cyclopentyloxybenzamide,
N-(2-Methyl-1,2,3,4-tetrahydroisoquinolin-7-yl)-4-cyclopropylmethoxybenzamide,
N-(2-Methyl-1,2,3,4-tetrahydroisoquinolin-7-yl)-3-cyano-4-methoxybenzamide,
N-(2-Methyl-1,2,3,4-tetrahydroisoquinolin-7-yl)-2-naphthamide,
N-(2-Methyl-1,2,3,4-tetrahydroisoquinolin-7-yl)-3-bromo-4-methybenzamide,
N-(2-Methyl-1,2,3,4-tetrahydroisoquinolin-7-yl)-naphthalene-1-carboxamide,
N-(2-Methyl-1,2,3,4-tetrahydroisoquinolin-7-yl)-3-chloro-4-methoxybenzamide,
N-(2-Methyl-1,2,3,4-tetrahydroisoquinolin-7-yl)-4-tert-butoxybenzamide,
N-(2-Methyl-1,2,3,4-tetrahydroisoquinolin-7-yl)-4-n-propoxybenzamide,
N-(2-Methyl-1,2,3,4-tetrahydroisoquinolin-7-yl) benzotriazole-5-carboxamide,
N-(2-Methyl-1,2,3,4-tetrahydroisoquinolin-7-yl) benzothiazole-6-carboxamide,
N-(2-Methyl-1,2,3,4-tetrahydroisoquinolin-7-yl)-2,3-dihydrobenzofuran-5-carboxamide,
N-(2-Methyl-1,2,3,4-tetrahydroisoquinolin-7-yl)-2-methylbenzimidazole-5-carboxamide,
N-(2-Methyl-1,2,3,4-tetrahydroisoquinolin-7-yl)-3-chloro-4-iso-propoxybenzamide,
N-(2-Methyl-1,2,3,4-tetrahydroisoquinolin-7-yl)-3-bromo-4-ethoxybenzamide,
N-(2-Methyl-1,2,3,4-tetrahydroisoquinolin-7-yl)-3-chloro-4-ethoxybenzamide,
N-(2-Methyl-1,2,3,4-tetrahydroisoquinolin-7-yl)-4-methoxy-3-trifluoromethylbenzamide,
N-(2-Methyl-1,2,3,4-tetrahydroisoquinolin-7-yl)-3,5-dichloro-4-methoxybenzamide,
N-(2-Methyl)-1,2,3,4-tetrahydroisoquinolin-7-yl)-3,5-dichloro-4-ethoxybenzamide,
N-(2-Methyl)-1,2,3,4-tetrahydroisoquinolin-7-yl)-3,5-dichloro-4-iso-propoxybenzamide,
N-(2-Methyl-1,2,3,4-tetrahydroisoquinolin-7-yl)-3-methylsulfonylbenzamide,
N-(2-methyl-1,2,3,4-tetrahydroisoquinolin-7-yl)-3-bromo-4-tert-butylbenzamide,
N-(2-Methyl-1,2,3,4-tetrahydroisoquinolin-7-yl)-2-bromo-5-methoxybenzamide,
N-(2-Methyl-1,2,3,4-tetrahydroisoquinolin-7-yl)-4-fluoro-3-methoxybenzamide hydrochloride,
N-(2-Methyl-1,2,3,4-tetrahydroisoquinolin-7-yl)-1-methylpyrazole-4-carboxamide,
N-(2-Methyl-1,2,3,4-tetrahydroisoquinolin-7-yl)-4-trifluoromethylpyrazole-3-carboxamide,
N-(2-Methyl-1,2,3,4-tetrahydroisoquinolin-7-yl)-2-methylthiazole-4-carboxamide,
N-(2-Methyl-1,2,3,4-tetrahydroisoquinolin-7-yl)-5-methylisoxazole-3-carboxamide,
N-(2-Methyl-1,2,3,4-tetrahydroisoquinolin-7-yl)-5-tert-butylisoxazole-3-carboxamide,
N-(2-Methyl-1,2,3,4-tetrahydroisoquinolin-7-yl)-3-methoxyisoxazole-5-carboxamide hydrochloride,
N-(2-methyl-1,2,3,4-tetrahydroisoquinolin-7-yl)indole-2-carboxamide,
N-(2-Methyl-1,2,3,4-tetrahydroisoquinolin-7-yl)-3-bromo-4-iso-propylbenzamide hydrochloride,
N-(2-Methyl-1,2,3,4-tetrahydroisoquinolin-7-yl)-3-cyano-4-iso-propylbenzamide hydrochloride,
N-(2-Methyl-1,2,3,4-tetrahydroisoquinolin-7-yl)-3-fluoro-4-methoxybenzamide,
N-(2-Methyl-1,2,3,4-tetrahydroisoquinolin-7-yl)-3-cyano-4-n-propoxybenzamide,
N-(2-Methyl-1,2,3,4-tetrahydroisoquinolin-7-yl)-3-cyano-4-ethoxybenzamide,
N-(2-Methyl-1,2,3,4-tetrahydroisoquinolin-7-yl)-3-bromo-4-n-propoxybenzamide,
N-(2-Methyl-1,2,3,4-tetrahydroisoquinolin-7-yl)-3-bromo-4-ethylbenzamide,
N-(2-Methyl-1,2,3,4-tetrahydroisoquinolin-7-yl)-3-iodo-4-methoxybenzamide,
N-(2-Methyl-1,2,3,4-tetrahydroisoquinolin-7-yl)-4-iso-propoxy-3-trifluoromethylbenzamide,
N-(2-Methyl-1,2,3,4-tetrahydroisoquinolin-7-yl)-4-chloro-3-methoxybenzamide,
N-(2-Methyl-1,2,3,4-tetrahydroisoquinolin-7-yl)-4-n-propoxy-3-trifluoromethylbenzamide,
N-(2-Methyl-1,2,3,4-tetrahydroisoquinolin-7-yl)-3-chloro-4-tert-butylbenzamide hydrochloride,
N-(2-Methyl-1,2,3,4-tetrahydroisoquinolin-7-yl)-4-methoxybenzamide hydrochloride,
N-(2-Methyl-1,2,3,4-tetrahydroisoquinolin-7-yl)-4-fluoro-3-methylbenzamide hydrochloride,
N-(2-Methyl-1,2,3,4-tetrahydroisoquinolin-7-yl)-3-chloro-4-iso-propylbenzamide,
N-(2-Methyl-1,2,3,4-tetrahydroisoquinolin-7-yl)-3-cyano-4-ethylbenzamide hydrochloride,
N-(2-Methyl-1,2,3,4-tetrahydroisoquinolin-7-yl)-4-iso-propyl-3-trifluoromethyl-benzamide hydrochloride,
N-(2-Methyl-1,2,3,4-tetrahydroisoquinolin-7-yl)-4-ethyl-3-trifluoromethylbenzamide hydrochloride,
N-(2-Methyl-1,2,3,4-tetrahydroisoquinolin-7-yl)-3-cyano-4-iso-propoxybenzamide hydrochloride,
N-(1,2,3,4-Tetrahydroisoquinolin-7-yl)-4-methoxy-3-trifluoromethylbenzamide, N-(2-Methyl-1,2,3,4-tetrahydroisoquinolin-7-yl)-4-methyl-3-methylsulfonyl-benzamide,
N-(2-Methyl-1,2,3,4-tetrahydroisoquinolin-7-yl)-4-ethyl-3-methylsulfonylbenzamide,
N-(2-Methyl-1,2,3,4-tetrahydroisoquinolin-7-yl)-3-methylsulfonyl-4-iso-propylbenzamide,
N-(2-Methyl-1,2,3,4-tetrahydroisoquinolin-7-yl)-3-methylsulfonyl-4-methoxybenzamide,
N-(2-Methyl-1,2,3,4-tetrahydroisoquinolin-7-yl)-3-trifluoroacetylbenzamide hydrochloride,
N-(2-Methyl-1,2,3,4-tetrahydroisoquinolin-7-yl)-4-methoxy-3-pentafluoroethyl-benzamide hydrochloride,
N-(2-n-Propyl-1,2,3,4-tetrahydroisoquinolin-7-yl)-3-bromo-4-ethoxybenzamide,
N-(2-n-Propyl-1,2,3,4-tetrahydroisoquinolin-7-yl)-4-methoxy-3-trifluoromethylbenzamide,
N-(2-n-Propyl-1,2,3,4-tetrahydroisoquinolin-7-yl)-3-chloro-4-iso-propoxybenzamide,
N-(2-Methyl-1,2,3,4-tetrahydroisoquinolin-7-yl)-3-cyano-4-iso-butylbenzamide hydrochloride,
N-(2-Methyl-1,2,3,4-tetrahydroisoquinolin-7-yl)-4-iso-butyl-3-trifluoromethyl-benzamide hydrochloride,
N-(2-Ethyl-1,2,3,4-tetrahydroisoquinolin-7-yl)-3-bromo-4-ethoxybenzamide,
N-(2-Ethyl-1,2,3,4-tetrahydro-isoquinolin-7-yl)-4-methoxy-3-trifluoromethylbenzamide,
N-(2-iso-Propyl-1,2,3,4-tetrahydroisoquinolin-7-yl)-3-bromo-4-ethoxybenzamide,
N-(2-iso-Propyl-1,2,3,4-tetrahydroisoquinolin-7-yl)-4-methoxy-3-trifluoromethylbenzamide,
N-(2-Methyl-1,2,3,4-tetrahydroisoquinolin-7-yl)-4-ethoxy-3-methylsufonyl-benzamide,
N-(2-Methyl-1,2,3,4-tetrahydroisoquinolin-7-yl)-4-oxochroman-6-carboxamide hydrochloride,
N-(2-Formyl-1,2,3,4-tetrahydroisoquinolin-7-yl)-4-methoxy-3-trifluoromethylbenzamide,
N-(2-Hydroxyethyl-1,2,3,4-tetrahydroisoquinolin-7-yl)-3-bromo-4-ethoxybenzamide,
N-(2-Hydroxyethyl-1,2,3,4-tetrahydroisoquinolin-7-yl)-3-bromo-4-ethylbenzamide,
N-(2-Methyl-1,2,3,4-tetrahydroisoquinolin-7-yl)-4-phenylmethoxy-3-trifluoromethylbenzamide,
N-(2-Methyl-1,2,3,4-tetrahydroisoquinolin-7-yl)-4-hydroxy-3-trifluoromethylbenzamide,
N-(2-Methoxyethyl-1,2,3,4-tetrahydroisoquinolin-7-yl)-3-bromo-4-iso-propoxybenzamide,
N-(2-Methoxyethyl-1,2,3,4-tetrahydroisoquinolin-7-yl)-3-chloro-4-iso-propoxybenzamide,
N-(2-Methoxyethyl-1,2,3,4-tetrahydroisoquinolin-7-yl)-4-methoxy-3-trifluoromethylbenzamide,
N-(5-Iodo-1,2,3,4-tetrahydroisoquinolin-7-yl)-4-azidobenzamide trifluoroacetate,
N-(2-Methyl-5-trifluoroacetylamino-1,2,3,4-tetrahydroisoquinolin-7-yl)-3-bromo-4-methoxybenzamide,
N-(2-Methyl-5-chloro-1,2,3,4-tetrahydroisoquinolin-7-yl)-3-bromo-4-ethoxybenzamide, or
N-(2-Methyl-5-chloro-1,2,3,4-tetrahydroisoquinolin-7-yl)-3-bromo-4-ethylbenzamide;
or a pharmaceutically acceptable salt thereof.

6. The method according to claim 1 wherein the compound is selected from the compounds of claim 5.

7. A pharmaceutical composition which comprises a compound as defined in claim 5, or a pharmaceutically acceptable salt or solvate thereof, and a pharmaceutically acceptable carrier.

8. A method of treatment of disorders treatable and/or preventable with anti-convulsive agents, migraine, neuralgia, trigeminal neuralgia, neuropathic pain, dental pain, and cancer pain comprising administering to the sufferer in need thereof an effective amount of a compound of claim 5 or a pharmaceutically acceptable salt thereof.

9. A pharmaceutical composition for use in the treatment of disorders treatable and/or preventable with anti-convulsive agents, migraine, neuralgia, trigeminal neuralgia, neuropathic pain, dental pain, and cancer pain which comprises a compound of formula I

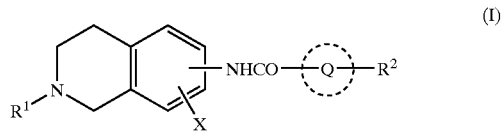

(I)

wherein:
Q is a monocyclic or bicyclic aryl or heteroaryl ring;
$R^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO$_2$—;
$R^2$ is hydrogen, hydroxy or up to three substituents selected from halogen, $NO_2$, CN, $N_3$, $CF_3O$—, $CF_3S$—, $CF_3CO$—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, acetoxy, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl)NHSO$_2$—, $(C_{1-4}$alkyl$)_2$NCO—, $(C_{1-4}$alkyl)NHCO— or $CONH_2$; or —$NR^3R^4$ where $R^3$ is hydrogen or $C_{1-4}$alkyl, and $R^4$ is hydrogen, $C_{1-4}$alkyl, formyl, —$CO_2C_{1-4}$alkyl or —$COC_{1-4}$alkyl; or two $R^2$ groups together form a carbocyclic ring that is saturated or unsaturated and unsubstituted or substituted by —OH or =O; and
X is hydrogen, halogen, $C_{1-6}$alkoxy, $C_{1-6}$alkyl, amino or trifluoroacetylamino;
provided:
when X is hydrogen, $R^2$ is not 2-alkoxy; and
when X is halogen the compound of formula (I) is not N-(7-iodo-2-methyl-1,2,3,4-tetrahydroisoquinolin-5-yl)-5-benzoyl-2-methoxybenzamide, N-(7-iodo-1,2,3,4-tetrahydroisoquinolin-5-yl)-5-benzoyl-2-methoxybenzamide, N-(5-iodo-1,2,3,4-tetrahydroisoquinolin-7-yl)-5-benzoyl-2-methoxybenzamide, N-(5-iodo-1,2,3,4-tetrahydroisoquinolin-7-yl)-2-methoxy-4-trifluoromethyldiazirinylbenzamide, N-(5-iodo-1,2,3,4-tetrahydroisoquinolin-7-yl)-2-methoxy-5-trifluoromethyldiazirinylbenzamide, N-(7-iodo-1,2,3,4-tetrahydroisoquinolin-5-yl)-2-methoxy-5-trifluoromethyldiazirinylbenzamide or N-(8-fluoro-2-methyl-1,2,3,4-tetrahydroisoquinolin-5-yl)-4-t-butyl-2-methoxybenzamide;
or a pharmaceutically acceptable salt or solvate thereof, and a pharmaceutically acceptable carrier.

10. A method of treatment of disorders treatable and/or preventable with anti-convulsive agents, migraine, neuralgia, trigeminal neuralgia, neuropathic pain, dental pain, and cancer pain comprising administering to the sufferer in need thereof, an effective amount of a compound of formula (I), or a pharmaceutically acceptable salt thereof:

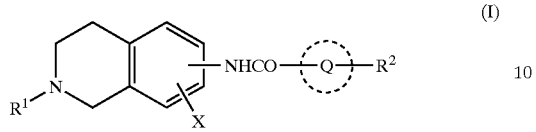

(I)

wherein:

Q is a monocyclic or bicyclic aryl or heteroaryl ring;

$R^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO$_2$—;

$R^2$ is hydrogen, hydroxy or up to three substituents selected from halogen, $NO_2$, CN, $N_3$, $CF_3O$—, $CF_3S$—, $CF_3CO$—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkyl)CO—, acetoxy, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl$)$NHSO$_2$—, $(C_{1-4}$alkyl$)_2$NCO—, $(C_{1-4}$alkyl$)$NHCO— or $CONH_2$; or —$NR^3R^4$ where $R^3$ is hydrogen or $C_{1-4}$alkyl, and $R^4$ is hydrogen, $C_{1-4}$alkyl, formyl, —$CO_2C_{1-4}$alkyl or —$COC_{1-4}$alkyl; or two $R^2$ groups together form a carbocyclic ring that is saturated or unsaturated and unsubstituted or substituted by —OH or =O; and X is hydrogen, halogen, $C_{1-6}$alkoxy, $C_{1-6}$alkyl, amino or trifluoroacetylamino;

provided:

when X is hydrogen, $R^2$ is not 2-alkoxy; and when X is halogen the compound of formula (I) is not N-(7-iodo-2-methyl-1,2,3,4-tetrahydroisoquinolin-5-yl)-5-benzoyl-2-methoxybenzamide, N-(7-iodo-1,2,3,4-tetrahydroisoquinolin-5-yl)-5-benzoyl-2-methoxybenzamide, N-(5-iodo-1,2,3,4-tetrahydroisoquinolin-7-yl)-5-benzoyl-2-methoxybenzamide, N-(5-iodo-1,2,3,4-tetrahydroisoquinolin-7-yl)-2-methoxy-4-trifluoromethyldiazirinylbenzamide, N-(5-iodo-1,2,3,4-tetrahydroisoquinolin-7-yl)-2-methoxy-5-trifluoromethyldiazirinylbenzamide, N-(7-iodo-1,2,3,4-tetrahydroisoquinolin-5-yl)-2-methoxy-5-trifluoromethyldiazirinyl benzamide or N-(8-fluoro-2-methyl-1,2,3,4-tetrahydroisoquinolin-5-yl)-4-t-butyl-2-methoxybenzamide.

11. A method according to claim 10 wherein the compound of formula (I) is chosen from the compounds of formula (IA) or (IB):

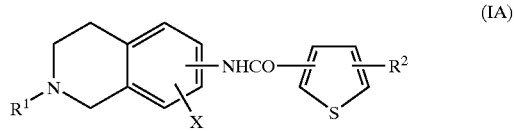

(IA)

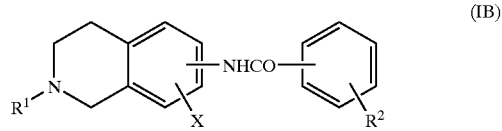

(IB)

wherein $R^1$, $R^2$ and X are as defined in claim 10.

* * * * *